(12) United States Patent
Takumi et al.

(10) Patent No.: US 10,077,432 B2
(45) Date of Patent: Sep. 18, 2018

(54) FLAVIN-CONJUGATED GLUCOSE DEHYDROGENASE

(71) Applicant: IKEDA FOOD RESEARCH CO., LTD., Hiroshima (JP)

(72) Inventors: Takafumi Takumi, Hiroshima (JP); Mizuki Shigeshiro, Hiroshima (JP); Daisuke Sato, Hiroshima (JP)

(73) Assignee: IKEDA FOOD RESEARCH CO., LTD., Hiroshima (JP)

( * ) Notice: Subject to any disclaimer, the term of this patent is extended or adjusted under 35 U.S.C. 154(b) by 48 days.

(21) Appl. No.: 15/126,665

(22) PCT Filed: Mar. 19, 2015

(86) PCT No.: PCT/JP2015/058171
§ 371 (c)(1),
(2) Date: Sep. 16, 2016

(87) PCT Pub. No.: WO2015/141761
PCT Pub. Date: Sep. 24, 2015

(65) Prior Publication Data
US 2017/0088823 A1 Mar. 30, 2017

(30) Foreign Application Priority Data
Mar. 21, 2014 (JP) ................. 2014-059315

(51) Int. Cl.
*C12N 9/04* (2006.01)
*C12N 9/96* (2006.01)
*C12Q 1/54* (2006.01)
*C12Q 1/32* (2006.01)

(52) U.S. Cl.
CPC ............ *C12N 9/0006* (2013.01); *C12N 9/96* (2013.01); *C12Q 1/32* (2013.01); *C12Q 1/54* (2013.01); *C12Y 101/9901* (2013.01); *G01N 2333/904* (2013.01)

(58) Field of Classification Search
CPC .. G01N 2333/904; C12N 9/0006; C12N 9/96; C12Y 101/9901; C12Q 1/32; C12Q 1/54
See application file for complete search history.

(56) References Cited

U.S. PATENT DOCUMENTS

| | | |
|---|---|---|
| 2005/0191627 A1 | 9/2005 | Yang et al. |
| 2006/0063217 A1 | 3/2006 | Omura et al. |
| 2008/0014612 A1 | 1/2008 | Tsuji et al. |
| 2008/0020426 A1 | 1/2008 | Aiba et al. |
| 2009/0155848 A1 | 6/2009 | Aiba et al. |
| 2009/0259024 A1 | 10/2009 | Tsuji et al. |
| 2011/0033880 A1 | 2/2011 | Yada et al. |
| 2011/0318810 A1 | 12/2011 | Tajima et al. |
| 2012/0122130 A1 | 5/2012 | Omura et al. |
| 2013/0122149 A1 | 5/2013 | Toscano et al. |
| 2013/0203093 A1 | 8/2013 | Honda et al. |
| 2014/0154777 A1 | 6/2014 | Sumida et al. |
| 2014/0287478 A1 | 9/2014 | Sumida et al. |
| 2014/0302542 A1* | 10/2014 | Araki ............... C12Q 1/32 435/14 |
| 2015/0031059 A1 | 1/2015 | Sumida et al. |
| 2015/0111280 A1 | 4/2015 | Sumida et al. |
| 2015/0152394 A1 | 6/2015 | Honda et al. |
| 2015/0240216 A1 | 8/2015 | Yamazaki et al. |
| 2015/0267178 A1 | 9/2015 | Ozawa et al. |

FOREIGN PATENT DOCUMENTS

| | | |
|---|---|---|
| JP | 2013-90620 | 5/2013 |
| WO | 2004/058958 | 7/2004 |
| WO | 2006/101239 | 9/2006 |
| WO | 2007/116710 | 10/2007 |
| WO | 2008/001903 | 1/2008 |
| WO | 2013/031664 | 3/2013 |
| WO | 2013/051704 | 4/2013 |
| WO | WO 2013/065770 | * 5/2013 |
| WO | 2013/147206 | 10/2013 |

OTHER PUBLICATIONS

Witkowski et al., Biochemistry 38:11643-11650, 1999.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Douglas R. Cavener "GMC Oxidoreductases A Newly Defined Family of Homologous Proteins with Diverse Catalytic Activities", J. Mol. Biol. (1992), 223, 811-814.
Kazushige Mori et al., "Screening of *Aspergillus*-derived FAD-glucose dehydrogenases from fungal genome database", Biotechnol Lett (2011)33(11) 2255-2263.
Christoph Sygmund et al., "Heterologous overexpression of Glomerella cingulata FAD-dependent glucose dehydrogenase in *Escherichia coli* and Pichi pastoris", Microbial Cell Factories (2011)10(1) 106.
Cheeseman et al. GenBank_CDM29258, 2014.
International Search Report dated May 12, 2015 in International Application No. PCT/JP2015/058171.

* cited by examiner

*Primary Examiner* — Delia M Ramirez
(74) *Attorney, Agent, or Firm* — Wenderoth, Lind & Ponack, L.L.P.

(57) ABSTRACT

A flavin-conjugated glucose dehydrogenase which is composed of proteins having the following amino acid sequence (a), (b) or (c), and having glucose dehydrogenase activity: (a) an amino acid sequence represented by SEQ ID NO: 2, 3, 5, 6, 8 or 9; (b) an amino acid sequence in which one or more amino acids are deleted from, replaced in or added to the amino acid sequence represented by SEQ ID NO: 2, 3, 5, 6, 8 or 9; (c) an amino acid sequence having at least 85% identity with the amino acid sequence represented by SEQ ID NO 2 or 3, at least 95% identity with the amino acid sequence represented by SEQ ID NO 5 or 6, or at least 80% identity with the amino acid sequence represented by SEQ ID NO 8 or 9.

5 Claims, 2 Drawing Sheets
Specification includes a Sequence Listing.

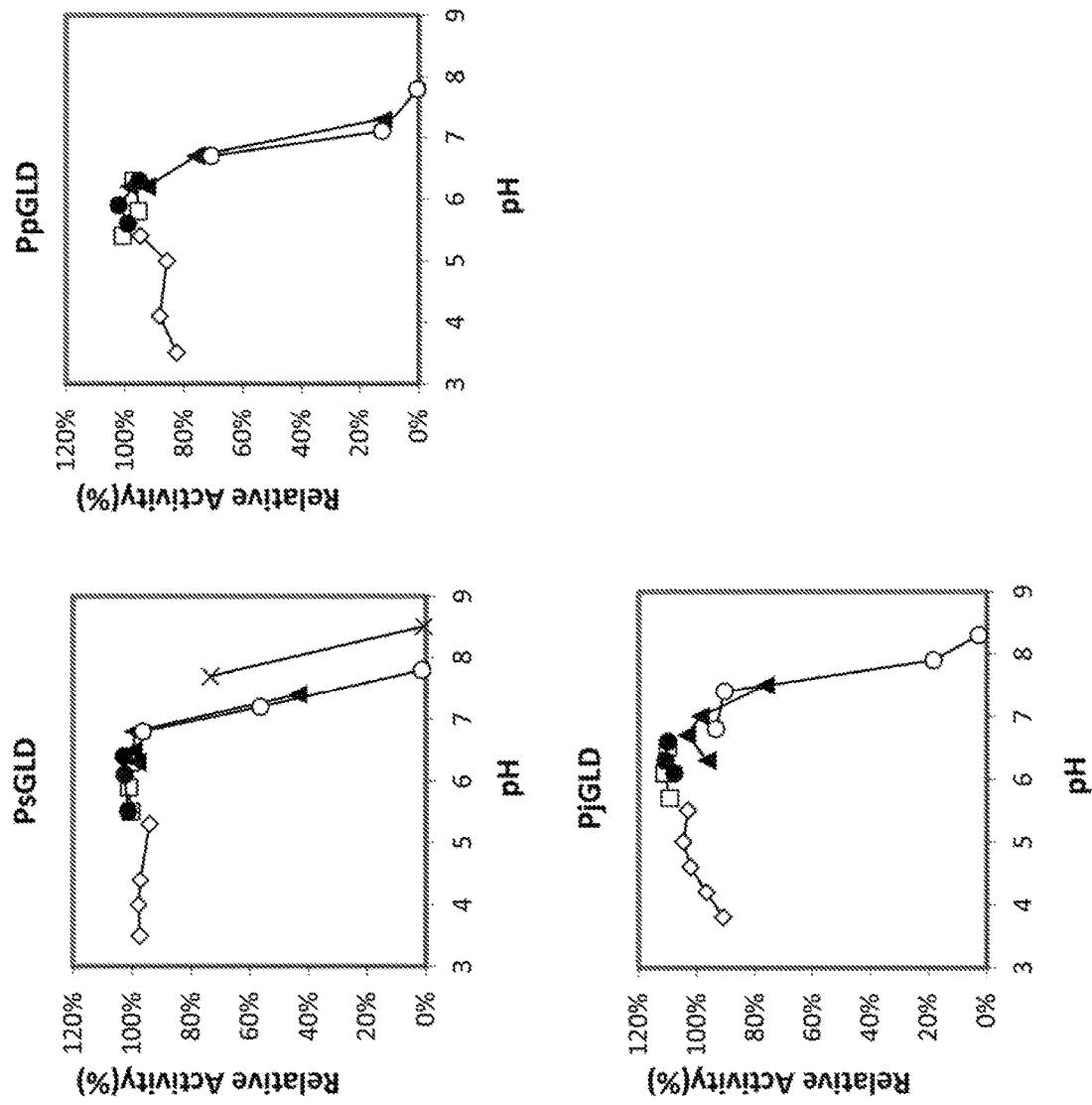
[Figure 1]

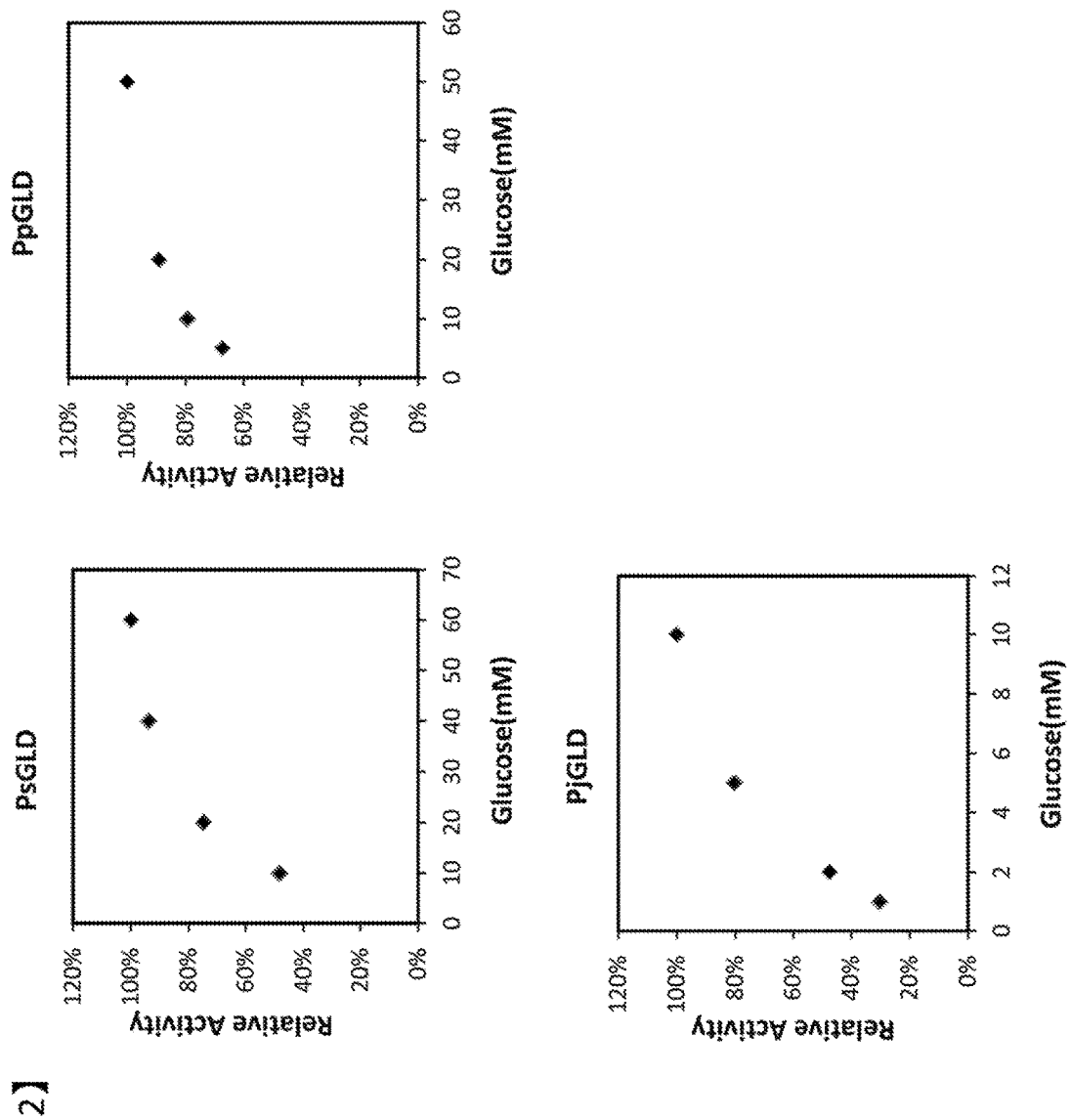
[Figure 2]

FLAVIN-CONJUGATED GLUCOSE DEHYDROGENASE

TECHNICAL FIELD

The present invention relates to a glucose dehydrogenase, a polynucleotide encoding the enzyme, a method for manufacturing the enzyme, a method for measuring glucose using the enzyme, a measuring reagent composition, a biosensor and the like.

BACKGROUND ART

Measurement of a blood glucose (blood sugar) concentration is important primarily in blood sugar control for a diabetes patient. For measuring blood sugar, biosensors are widely used as blood sugar meters utilizing enzymes.

As enzymes usable for biosensors, glucose oxidases and glucose dehydrogenases are known. However, the glucose oxidases had problems that measurement errors are caused by dissolved oxygen in the blood. Among the glucose dehydrogenases, flavin-conjugated glucose dehydrogenases derived from eukaryotic cells are not affected by dissolved oxygen, require no addition of coenzymes, and have an excellent substrate specificity, and thus they are useful as enzymes for biosensors (Patent Documents 1 to 6).

PRIOR ART DOCUMENTS

Patent Documents

Patent Document 1: International Publication WO 2004/058958 pamphlet
Patent Document 2: International Publication WO 2006/101239 pamphlet
Patent Document 3: International Publication WO No. 2008/001903 pamphlet
Patent Document 4: International Publication WO No. 2007/116710 pamphlet
Patent Document 5: International Publication WO No. 2013/031664 pamphlet
Patent Document 6: International Publication WO No. 2013/147206 pamphlet

SUMMARY OF INVENTION

Problem to be Solved

The present invention provides a novel glucose dehydrogenase, a polynucleotide encoding the enzyme, a method for manufacturing the enzyme, a method for measuring glucose using the enzyme, a measuring reagent composition and a biosensor. Furthermore, the object of the present invention is to provide a method for manufacturing the measuring reagent composition and a method for manufacturing the biosensor.

Solution to Problem

The inventors searched various microorganism-derived glucose dehydrogenases, and then found a novel flavin-conjugated glucose dehydrogenase from microorganisms belonging to *Penicillium*. Furthermore, the inventors found an efficient method for manufacturing the flavin-conjugated glucose dehydrogenase to complete the present invention.

That is, the present invention relates to the following aspects [1] to [12].

[1] A flavin-conjugated glucose dehydrogenase which is composed of proteins having the following amino acid sequence (a), (b) or (c), and having glucose dehydrogenase activity:
 (a) an amino acid sequence represented by SEQ ID NO: 2, 3, 5, 6, 8 or 9;
 (b) an amino acid sequence in which one or more amino acids are deleted from, replaced in or added to the amino acid sequence represented by SEQ ID NO: 2, 3, 5, 6, 8 or 9;
 (c) an amino acid sequence having at least 85% identity with the amino acid sequence represented by SEQ ID NO 2 or 3, at least 95% identity with the amino acid sequence represented by SEQ ID NO 5 or 6, or at least 80% identity with the amino acid sequence represented by SEQ ID NO 8 or 9.
[2] The flavin-conjugated glucose dehydrogenase according to [1] having the following properties:
 (1) action: oxidizing a hydroxyl group at position 1 of glucose in the presence of an electron acceptor;
 (2) soluble;
 (3) activity on maltose is at most 1.5% when activity on glucose is taken to be 100%;
 (4) a molecular weight of a polypeptide of the enzyme is 60 to 70 kDa; and
 (5) stable at pH 3.8.
[3] The flavin-conjugated glucose dehydrogenase according to [1] or [2], (6) which is derived from microorganisms belonging to *Penicillium*.
[4] A polynucleotide consisting of the following (i), (ii), (iii), (iv) or (v):
 (i) a polynucleotide which encodes proteins according to [1];
 (ii) a polynucleotide which has a base sequence represented by SEQ ID NO: 1, 4 or 7;
 (iii) a polynucleotide which has a base sequence in which one or more bases are deleted from, replaced in or added to the base sequence represented by SEQ ID NO: 1, 4 or 7, and encodes a protein having a glucose dehydrogenase activity;
 (iv) a polynucleotide which hybridizes with the polynucleotide having the base sequence represented by SEQ ID NO: 1, 4 or 7 under stringent conditions, and encodes proteins having the glucose dehydrogenase activity;
 (v) a polynucleotide which has a base sequence having at least 80% identity with the base sequence represented by SEQ ID NO 1, 4 or 7, and encodes a protein having the glucose dehydrogenase activity.
[5] The polynucleotide according to [4] derived from microorganisms belonging to *Penicillium*.
[6] A recombinant vector containing the polynucleotide according to [4] or [5].
[7] A transformant which was transformed with the vector according to [6].
[8] A method for manufacturing a flavin-conjugated glucose dehydrogenase, comprising culturing the cell according to [7], and collecting the flavin-conjugated glucose dehydrogenase from the culture.
[9] A flavin-conjugated glucose dehydrogenase obtained by the manufacturing method according to [8].
[10] A method for measuring glucose, using the flavin-conjugated glucose dehydrogenase according to any one of [1] to [3] and [9].
[11] A glucose measuring reagent composition, containing the flavin-conjugated glucose dehydrogenase according to any one of [1] to [3] and [9].
[12] A biosensor for measuring glucose, containing the flavin-conjugated glucose dehydrogenase according to any one of [1] to [3] and [9].

Advantages of the Invention

The present invention provided a novel flavin-conjugated glucose dehydrogenase and further facilitated the manufacture of the enzyme. It became possible to measure glucose using the enzyme and to manufacture the glucose measuring reagent composition and the biosensor for measuring glucose containing the enzyme.

BRIEF DESCRIPTION OF DRAWINGS

FIG. 1 shows pH stability.
FIG. 2 shows results from measurements of D-glucose.

DESCRIPTION OF EMBODIMENTS

A glucose dehydrogenase according to the present invention is a protein having the following amino acid sequence (a), (b) or (c), and having glucose dehydrogenase activity. The "protein" includes a glycoprotein.
  (a) An amino acid sequence represented by SEQ ID NO: 2, 3, 5, 6, 8 or 9.
  (b) An amino acid sequence in which one or more amino acids are deleted from, replaced in or added to the amino acid sequence represented by SEQ ID NO: 2, 3, 5, 6, 8 or 9. The number of variations is preferably at most 60, 55, 50, 40, 30, 20, 15, 10, 5, 3, or 2.
  (c) An amino acid sequence having at least 80%, preferably at least 85%, 90%, 92%, 95%, 97%, 98% or 99% identity with the amino acid sequence represented by SEQ ID NO: 2, 3, 5, 6, 8 or 9.

The enzyme is a protein preferably composed of the amino acid sequence (a), (b) or (c) and having glucose dehydrogenase activity.

The glucose dehydrogenase of the present invention is not particularly limited as long as it is a protein having the above-described sequences, and it may also be an enzyme derived from a wild strain, a recombinant enzyme obtained by gene recombination, or a synthetic enzyme obtained by synthesis. Preferably, it is the recombinant enzyme.

The flavin-conjugated glucose dehydrogenase of the present invention preferably has the following properties (1) to (8). The flavin may include a flavin adenine dinucleotide (FAD) and a flavin mononucleotide (FMN), and the FAD is preferable.

(1) action: the enzyme oxidizes a hydroxyl group at position 1 of glucose in the presence of an electron acceptor.
(2) soluble.
(3) The substrate specificity is excellent. When activity on 50 mM of glucose is taken to be 100%, activity on 50 mM of maltose is at most 3.0%, preferably at most 2.5%, 2.0% or 1.5%. When activity on 50 mM of glucose is taken to be 100%, activity on 50 mM of xylose is preferably at most 3.0%, more preferably at most 20% or 15%. By having said substrate specificity, the enzyme is not susceptible to impurities during the measurement, and correct measurement can be achieved.
(4) A molecular weight of a polypeptide of the enzyme is 60-70 kDa. Preferably, it is 65-70 kDa. The molecular weight of the polypeptide of the enzyme means a molecular weight of a protein moiety from which sugar chains were removed, measured by a SDS-polyacrylamide gel electrophoresis method. For the molecular weight of whole enzyme measured by the SDS-polyacrylamide gel electrophoresis method, the molecular weight is changed as the amount of the added sugar chains is changed depending on its culture condition, purification condition, etc., and in the case of a recombinant enzyme, the presence or absence of the sugar chain and the amount of the added sugar are changed and the molecular weight varies also depending on its host cell or the like.
(5) Preferably the enzyme is stable in an acidic range. More preferably, the enzyme is stable at pH 3.8, and even more preferably at pH 3.8 to 6.7. Preferably the enzyme has at least 80% of remaining activity at pH 3.8, and more preferably at least 70% of remaining activity at pH 3.8 to 6.7. Note that the remaining activity is relative activity after treatment in 100 mM of various buffers at 30° C. for 1 hour, when the enzyme activity before treatment is taken to be 100%. By having such stability, the enzyme can be stably used even in the acidic range.
(6) Preferably the enzyme is derived from microorganisms belonging to *Penicillium*. The microorganism can be exemplified by *Penicillium sclerotiorum*, *Penicillium paneum* or *Penicillium janthinellum*. Also, the glucose dehydrogenase of the present invention may include recombinant glucose dehydrogenases produced by introducing DNAs or their partially modified DNAs artificially synthesized on the basis of genes encoding a glucose delydrogenase obtained from glucose dehydrogenase-producing microorganisms belonging *Penicillium* by known genetic engineering procedures or of the genetic information of the genes, into appropriate host microorganisms by various known procedures. Since *Penicillium* have been frequently used for industrial applications, they are easy to handle. Since *Penicillium* grow quickly, they can be cultured in a short period, and are considerably easy to use and useful as strains for screening, strains for obtaining genes or strains for producing enzymes.
(7) Its Km for glucose is preferably 1.0 to 25 mM, more preferably 1.5 to 20 mM, even more preferably at most 15 mM, 10 mM or 5 mM. Note that the Km is a value calculated according to Hanes-Woolf plot. The above-described Km allows correct measurement with a small amount of enzyme even in a low concentration range of substrate.
(8) When activity value at 37° C. is taken to be 100%, activity at 25° C. is preferably at least 50%. Such a temperature property can reduce changes in the enzyme activity due to temperature. Consequently, the enzyme is hardly affected by an environmental temperature during measurement, and thus correct measurement can be achieved.

The polynucleotide of the present invention consists of the following (i), (ii), (iii), (iv) or (v).
  (i) A polynucleotide which encodes amino acid sequences according to the above-described (a), (b) and (c).
  (ii) A polynucleotide which has a base sequence represented by SEQ ID NO: 1, 4 or 7.
  (iii) A polynucleotide which has a base sequence in which one or more bases are deleted from, replaced in or added to the base sequence represented by SEQ ID NO: 1, 4 or 7, and encodes proteins having a glucose dehydrogenase activity. The number of variations is preferably at most 10, 8, 5, 3 or 2.
  (iv) A polynucleotide which hybridizes with the polynucleotide having the base sequence represented by SEQ ID NO: 1, 4 or 7 under stringent conditions, and encodes a protein having the glucose dehydrogenase activity.
  (v) A polynucleotide which has a base sequence having at least 80%, preferably at least 85%, 90%, 92%, 95%, 97%, 98% or 99% identity with the base sequence represented by SEQ ID NO: 1, 4 or 7, and encodes a protein having the glucose dehydrogenase activity.

In the present invention, as the specific condition of the "hybridizes under stringent conditions" in hybridization, a condition can be exemplified that e.g. 50% of formamide, 5×SSC (150 mM of sodium chloride, 15 mM of trisodium citrate, 10 mM of sodium phosphate, 1 mM of ethylenediaminetetraacetic acid, pH 7.2), 5×Denhardt's solution, 0.1% of SDS, 10% of dextran sulfate, and 100 μg/mL of modified salmon sperm DNA were incubated at 42° C., and then the filter is washed in 0.2×SSC at 42° C.

The identity is based upon the values of identity calculated by the homology analysis between base sequences or between amino acid sequences with GENETYX (GENETYX CORPORATION).

The polynucleotide of the present invention is preferably obtained from microorganisms belonging to *Penicillium*. The microorganism can be exemplified by *Penicillium sclerotiorum, Penicillium paneum* or *Penicillium janthinellum*. As methods of obtaining the polynucleotide, the whole length of the gene encoding the glucose dehydrogenase may be obtained from the chromosomal DNA or mRNA of the microorganism by PCR or the like, or alternatively the whole length of the gene sequence may be artificially synthesized from genetic information described in SEQ ID NO 1, 4 or 7. Also, a polynucleotide which was prepared by partially modifying the polynucleotide obtained by those methods and encodes a glucose dehydrogenase is the polynucleotide of the present invention. Since *Penicillium* have been frequently used for industrial applications, they are easy to handle. The polynucleotide of the present invention may be a chromosomal DNA or a cDNA.

The recombinant vector of the present invention is a cloning vector or an expression vector, and the vector is arbitrarily selected and includes the polynucleotide of the present invention as an insert. As the insert, a polynucleotide for which the codon usage is optimized may be introduced according to a host cell. Furthermore, when the host is a prokaryotic cell, a gene including no intron is used. When the host is a eukaryotic cell, a gene including an intron may be used. An expression level of the recombinant protein may be improved by replacing a termination codon by a termination codon optimal for the host. When the initiation codon is not included in the insert side, the initiation codon is added to the insert side, or alternatively the initiation codon on the vector side may be utilized so as to select a vector which expresses as a fusion protein. The expression vector may be either a vector for eukaryotic cell expression or a vector for prokaryotic cell expression. Note that, as required, an expression-contributing polynucleotide such as a chaperon and a lysozyme can be introduced into a vector which is the same as and/or different from the polynucleotide of the present invention. Furthermore, the glucose dehydrogenase of the present invention can also be expressed by using a vector which can be express as a fusion protein to which various tags such as His tag, FLAG tag and GFP are added.

When a recombinant protein is expressed by a gram-negative bacterium such as *Escherichia coli* using a glucose dehydrogenase gene containing a sequence encoding a secretory signal sequence such as SEQ NO: 1, 4 or 7, the recombinant protein is shifted to a periplasm, and therefore productivity is low. Thus, if the recombinant protein is intended to be efficiently collected, a sequence from which a sequence encoding the signal sequence was deleted should be used. Particularly in the case of gram-negative bacteria, preferably a polynucleotide including no intron and no sequence encoding the signal sequence, e.g. a polynucleotide in which an initiation codon ATG is added to a polynucleotide encoding the amino acid sequence represented by SEQ NO: 3, 6 or 9. The expression vector can be exemplified by a pUC system, pBluescriptII, a pET expression system, a pGEX expression system, a pCold expression system, etc.

Meanwhile, when producing by expression in a eukaryotic cell, the glucose dehydrogenase gene containing a sequence encoding a secretory signal sequence such as SEQ NO: 1, 4 or 7 may be inserted as a whole into a vector. Alternatively, a polynucleotide may also be adapted in which a sequence encoding the signal sequence is replaced by a sequence suitable for the host, for example. Furthermore, a sequence encoding a signal sequence on the vector side may be utilized. The expression vector can be exemplified by pKA1, pCDM8, pSVK3, pSVL, pBK-CMV, pBK-RSV, EBV vector, pRS, pYE82, etc.

The secretory signal sequence can be presumed by comparing with e.g. a signal sequence of glucose dehydrogenase sequences derived from *Aspergillus terreus* described in WO 2006/101239 (amino acid sequences shown in positions 1-19 of SEQ ID No: 2 in its publication). Furthermore, it can also be presumed by using a signal sequence-predicting site (e.g., Signal P: cbs.dtu.dk/services/SignalP/). For example, MKGFSGLALLPLAAAIPHASR for SEQ NO: 2, MRS-LIGLALLPLAVAVPHASHK for SEQ NO: 5, and MLVP-KTLSSVYFAAVAAAA for SEQ NO: 8 can be presumed as the signal sequence.

As the transformant of the present invention, e.g. prokaryotic cells such as *Escherichia coli* and *Bacillus subtilis*, eukaryotic cells such as *Eumycetes* (yeast, ascomycete such as *Aspergillus, basidiomycete*, etc.), insect cell and mammal cell, etc. can be used, and obtained by transformation with the vector of the present invention. The vector may be preserved in a transformant in a state like a plasmid, or may be preserved such that it is incorporated into a chromosome. Furthermore, although the host can be appropriately selected according to necessities of sugar chains and other peptide modifications, preferably a host capable of adding a sugar chain is selected to produce an enzyme having a sugar chain.

A glucose dehydrogenase can be collected from a culture obtained by culturing the transformant of the present invention to manufacture a recombinant glucose dehydrogenase.

For culturing microorganisms used in the present invention, conventional medium for culturing microorganisms can be used. Either a synthesized medium or a natural medium may be used, as long as the medium moderately contains carbon sources, nitrogen sources, minerals and other micronutrients required by the microorganisms of use. As the carbon sources, glucose, sucrose, dextrin, starch, glycerol, molasses, etc. can be used. As the nitrogen sources, inorganic salts such as ammonium chloride, ammonium nitrate, ammonium sulfate and ammonium phosphate, amino acids such as DL-alanine and L-glutamic acid, nitrogen-containing natural products such as peptone, meat extract, yeast extract, malt extract and corn steep liquor can be used. As the minerals, monosodium phosphate, disodium phosphate, monopotassium phosphate, dipotassium phosphate, magnesium sulfate, ferric chloride, etc. can be used.

The culturing for obtaining the glucose dehydrogenase of the present invention should be generally carried out under an aerobic condition by a method such as shake culture and aeration agitation. A culture condition suitable for production of the glucose dehydrogenase should be set in consideration of the properties of a glucose dehydrogenase-producing bacterium. For example, the culturing is carried out preferably at a culture temperature of 20° C. to 50, in a range of pH 4 to pH 8, and the pH may be adjusted during the culture in consideration of producibility. The culture period is preferably 2 to 10 days. By culturing with such a method, the glucose dehydrogenase can be produced and accumulated in a culture.

For the method for obtaining the glucose dehydrogenase from a culture, a conventional method for manufacturing proteins can be used. For example, first, a glucose dehydrogenase-producing bacterium is cultured, and then a culture supernatant is obtained by centrifugation. Alternatively, the cultured fungus body is obtained, the cultured microorganism is crushed by an appropriate manner, and supernatants are obtained from the crushed liquid by centrifugation or the like. Next, the glucose dehydrogenase contained in these supernatants can be purified by a conventional method for purifying proteins to obtain a purified enzyme. For example, the glucose dehydrogenase can be purified by combining purifying manipulations such as ultrafiltration, salt precipitation, solvent precipitation, heat treatment, dialysis, ion-exchange chromatography, hydrophobic chromatography, gel filtration and affinity chromatography.

Glucose can be measured by using the glucose dehydrogenase of the present invention. The method for measuring glucose of the present invention can include a step for bringing the test sample containing glucose into contact with the glucose dehydrogenase of the present invention, so as to quantify glucose in a test sample. Although the object to be measured in the present invention is not particularly limited, it can be exemplified by biological samples, specifically blood samples. The enzyme of the present invention is useful particularly for measuring blood sugar.

The present invention provides a reagent composition-manufacturing method for manufacturing a glucose measuring reagent composition using the glucose dehydrogenase of the present invention, or a biosensor-manufacturing method for manufacturing a biosensor for measuring glucose. In the manufacturing methods, pH may be preferably maintained in a range of 3.8 or higher, more preferably in a range of pH 3.8 to 6.7, but it is not limited to these ranges when the stability of the enzyme can be maintained by a stabilizer or the like.

The reagent composition of the present invention may be any reagent composition as long as it contains the glucose dehydrogenase of the present invention as an enzyme. The amount of the enzyme in the composition is not particularly limited as long as the object to be measured can be measured, but it is preferably about 0.05 to 50 U, more preferably about 0.1 to 20 U. The composition may suitably contain any other optional components known to those skilled in the art such as a stabilizer or a buffer to enhance thermal stability and storage stability of the enzyme and reagent components. The composition can be exemplified by a bovine serum albumin (BSA) or egg albumin, a sugar or a sugar alcohol not interactive with the enzyme, a carboxyl group-containing compound, an alkaline earth metal compound, an ammonium salt, sulfate, proteins or the like. Furthermore, a known substance which reduces the influence from impurities affecting the measurement in the test sample may also be contained in the measuring reagent.

The biosensor of the present invention may be any sensor as long as it contains the glucose dehydrogenase of the present invention as an enzyme in a reaction layer. For example, an electrochemical biosensor is made by forming an electrode system comprising an antipode and a working electrode on an insulating substrate using a method such as screen printing and vapor deposition, and further by providing the enzyme and a mediator. The mediator can be exemplified by a proteinic electronic mediator such as heme, a ferricyanide compound, a quinone compound, an osmium compound, a phenazine compound, a phenothiazine compound, etc. Moreover, a biosensor adapted to detecting ion change, coloring intensity, pH change or the like can also be constituted.

Furthermore, the glucose dehydrogenase of the present invention can be used for a bio battery. The bio battery of the present invention is composed of an anode electrode for oxidation reaction and a cathode electrode for reduction reaction, and optionally includes an electrolyte layer which separates between the anode and the cathode as required. An enzyme electrode containing the electron mediators and the glucose dehydrogenase is used for the anode electrode, electrons generated by oxidation of the substrate are collected on the electrode, and protons are generated. Meanwhile, an enzyme to be generally used for the cathode electrode may be used on the cathode side, for example laccase, ascorbate oxidase or bilirubin oxidase is used, and the proton generated on the anode side is reacted with oxygen to generate water. As the electrode, electrodes generally used for the bio battery, such as carbon, gold and platinum can be used.

In measuring the activity of the enzyme of the present invention, the enzyme is optionally diluted to a final concentration of preferably 0.15-0.6 U/mL for use. Note that a unit of enzyme activity of the enzyme (U) means an enzyme activity for oxidizing 1 μmol of glucose in one minute. The enzyme activity of the glucose dehydrogenase of the present invention can be measured by the following method.

(Method for Measuring Glucose Dehydrogenase (GLD) Activity)

1.00 mL of 100 mM potassium phosphate buffer (pH 6.0), 1.00 mL of 1 M D-glucose solution, 0.14 mL of 3 mM 2,6-dichlorophenolindophenol (hereinafter called DCIP), and 0.20 mL of 3 mM 1-methoxy-5-methylphenazinium methylsulfate, as well as 0.61 mL of ultrapure water were mixed, kept at 37° C. for 10 minutes, and then 0.05 mL of enzyme solution was added, and the reaction was initiated. For 5 minutes from the initiation of the reaction, a decrement per one minute of the absorbance at 600 nm ($\Delta A600$) associated with progression of the enzyme reaction was measured to calculate the enzyme activity from a straight part according to the following formula. In this measurement, for the enzyme activity, an enzyme amount for reducing 1 μmol of DCIP at 37° C., pH 6.0 per one minute was defined as 1 U.

$$\text{Glucose dehydrogenase (GLD) activity (U/mL)} = \\ (-(\Delta A600 - \Delta A600\text{blank}) \times 3.0 \times \text{dilution ratio of enzyme})/(10.8 \times 1.0 \times 0.05)$$

Note that, in the formula, 3.0 represents a liquid volume (mL) of the reaction reagent+the enzyme solution, 10.8 represents a molar absorption coefficient of DCIP at pH 6.0, 1.0 represents an optical path length (cm) of a cell, 0.05 represents a liquid volume (mL) of the enzyme solution, and $\Delta A600\text{blank}$ represents a decrement of the absorbance at 600 nm per minute in the case that the reaction is initiated by adding a dilute solution of the enzyme instead of the enzyme solution.

EXAMPLES

Hereinafter, the present invention will be specifically explained by Examples. However, the present invention is not limited by the following Examples.

Example 1

(Obtaining the Flavin-Conjugated Glucose Dehydrogenase (GLD))

GLD-producing bacteria isolated from the natural world were searched. As a result, GLD activity has been confirmed in the culture supernatants of three strains. Result of identification of the strains showed that the strains were *Penicillium sclerotiorum*, *Penicillium paneum* and *Penicillium janthinellum*. Respective enzymes derived from these GLD-producing bacteria were cloned.

(1) Culture of Fungus Bodies 150 mL of a liquid medium consisting of 2% (w/v) of Pinedex (Matsutani Chemical Industry Co., Ltd.), 1% (w/v) of tripton (Becton, Dickinson and Company), 0.5% (w/v) of potassium dihydrogenphosphate (NACALAI TESQUE, INC.), 0.05% (w/v) of magnesium sulfate heptahydrate (NACALAI TESQUE, INC.) and water was introduced into each of three Sakaguchi flasks with a 500 ml capacity, and autoclaved at 121° C. for 20 minutes. The GLD-producing bacteria were respectively inoculated to each cooled liquid medium, and shake-cultured at 25° C. for 72 hours, and then moist fungus bodies were respectively collected by means of bleached cloth.

(2) Isolation of the Total RNA

After 200 mg of each moist fungus body obtained in (1) was frozen at −80° C., 100 μg of the total RNA was extracted using ISOGENII (NIPPON GENE CO., LTD.).

(3) Preparation of a cDNA Library

Each cDNA library was prepared from each RNA obtained in (2) by a reverse transcription reaction, respectively, using a reverse transcriptase and an oligo dT primer with an adabtor sequence. "SMARTer RACE cDNA Amplification kit" (TAKARA BIO INC.) was used as a reaction reagent, and the reaction condition was adopted to a protocol described in an operating manual.

(4) Cloning of GLD Gene

Using each cDNA library obtained in (3) as a template, PCR was carried out by using a primer pair for obtaining GLD gene. As a result, PCR products considered to be internal sequences of the GLD gene were confirmed in all libraries. Note that the primer pair comprises primers designed for obtaining various GLD genes on the basis of a plurality of GLD sequences which have been already clarified by the present inventors. The PCR products is respectively purified, and ligated to T-vector PMD20 (TAKARA BIO INC.) by using DNA Ligation Kit (TAKARA BIO INC.).

Using each of the obtained plasmid vectors, each *Escherichia coli* JM109 competent cell (TAKARA BIO INC.) was transformed by a known method. Each plasmid vector was extracted/purified from each obtained transformant by using illustra plasmid-Prep Mini Spin Kit (GE Healthcare) to determine a base sequence of each insert. On the basis of each determined base sequence, each primer for clarifying upstream and downstream sequences of each GLD gene was designed. Using these primers, the whole length of each GLD gene was clarified by a 5' RACE method and a 3' RACE method.

The GLD gene sequences derived from *Penicillium sclerotiorum*, *Penicillium paneum* or *Penicillium janthinellum* were represented by SEQ ID NOs: 1, 4 or 7 respectively. Furthermore, the amino acid sequences expected from these gene sequences were represented by SEQ ID NO: 2, 5 or 8, respectively. SEQ ID NO: 3, 6 or 9 is a sequence in which a signal portion expected by Signal P4.1 is eliminated from the sequence of SEQ ID NO: 2, 5 or 8, respectively. Note that the *Penicillium sclerotiorum*-derived GLD is represented by PsGLD, the *Penicillium paneum*-derived GLD is represented by PpGLD, and the *Penicillium janthinellum*-derived GLD is represented by PjGLD.

(5) Preparation of Plasmid Vector for Expression Containing GLD Gene

A plasmid vector was prepared using an amylase-based modified promoter derived from *Aspergillus oryzae* described in Known Document 1 (heterologous gene expression system of *Aspergillus*, Toshitaka MINETOKI, Chemistry and Biology, 38, 12, 831-838, 2000). First, PCR was carried out using each cDNA library obtained in (3) as a template to obtain a PCR product containing each GLD gene. For amplification of the PsGLD gene, a primer pair of the following S158-Ori (SEQ ID NO: 10) and S158-R-1st (SEQ ID NO: 11) was used with a *Penicillium sclerotiorum*-derived cDNA as a template. For amplification of the PpGLD gene, a primer pair of the following SI 268-A.o (SEQ ID NO: 13) and S1268-R-1st (SEQ ID NO: 14) was used with a *Penicillium paneum*-derived cDNA as a template. For amplification of the PjGLD gene, a primer pair of the following T475-Ori (SEQ ID NO: 16) and T475-R-1st (SEQ ID NO: 17) was used with a *Penicillium janthinellum*-derived cDNA as a template. Next, PCR was carried out using each of the PCR products as a template to prepare each GLD gene for inserting vectors. For preparation of the PsGLD gene, a primer pair of S158-Ori (SEQ ID NO: 10) and SI 58-R-2nd (SEQ ID NO: 12) was used with a PCR product containing the PsGLD gene as a template. For preparation of the PpGLD gene, a primer pair of S1268-A.o (SEQ ID NO: 13) and S1268-R-2nd (SEQ ID NO: 15) was used with a PCR product containing the PpGLD gene as a template. For preparation of the PjGLD gene, a primer pair of T475-Ori (SEQ ID NO: 16) and T475-R-2nd (SEQ ID NO: 18) was used with a PCR product containing the PjGLD gene as a template.

Finally, the prepared PsGLD gene, PpGLD gene or PjGLD gene were bound to the downstream of the promoter to make each plasmid vector on which the gene could be expressed. Each of the made plasmid vector for expression was respectively introduced into *Escherichia coli* JM109 strain to transform it. Each of the resulting transformant was cultured, and each plasmid vector was extracted from each of the collected fungus bodies using illustra plasmid-Prep Mini Spin Kit. The sequence of each insert in the plasmid vector was analyzed, and then a base sequence including each GLD gene could be confirmed.

```
S158-Ori (SEQ ID NO: 10):
5'-(CCGCAGCTCGTCAAA)ATGAAGGGATTCTCGGGTC-3'
(in parentheses: transcription-enhancing factor)

S158-R-1st (SEQ ID NO: 11):
5'-((GTTCATTTA))GATCTTTCCCTTGATAATGTC-3'
(in double parentheses: pSEN vector sequence)

S158-R-2nd (SEQ ID NO: 12):
5'-((GTTACGCTTCTAGAGCATGCGTTCATTTA))GATCTTTCCC-3'
(in double parentheses: pSEN vector sequence
underlined: restriction enzyme site (SphI)

S1268-A.o (SEQ ID NO: 13):
5'-CCGGCTGGACGGGCCGTTCCCCATGCCTCACAAG-3'

S1268-R-1st (SEQ ID NO: 14):
5'-((GTTCATTTA))GTAGCACGCCTTGATGATAT-3'
(in double parentheses: pSEN vector sequence
```

-continued

S1268-R-2nd (SEQ ID NO: 15):
5'-((GTTACGCTTCTAGA<u>GCATGC</u>GTTCATTTA))GTAGCACGC-3'
(in double parentheses: pSEN vector sequence,
underlined: restriction enzyme site (SphI))

T475-Ori (SEQ ID NO: 16):
5'-(CCGCAGCTCGTCAAA)ATGCTGGTCCCCAAGACTC-3'
(in parentheses: transcription-enhancing factor)

T475-R-1st (SEQ ID NO: 17):
5'-((GTTCATTTA)AACGCTTCCAGCCTTGATC-3'
(in double parentheses; pSEN vector sequence)

T475-R-2nd (SEQ ID NO: 18):
5'-((GTTACGCTTCTAGA<u>GCATGC</u>GTTCATTTA))AACGCTTCCA-3'
(in double parentheses: pSEN vector sequence,
underlined: restriction enzyme site (SphI))

(6) Preparation of Transformant

Using the plasmid vector extracted in (5), a recombinant mold (*Aspergillus oryzae*) which produces each GLD was produced, respectively, according to methods described in Known Document 2 (Biosci. Biotech. Biochem., 61 (8), 1367-1369, 1997) and Known Document 3 (genetic engineering technique for koji-mold for sake, Katsuya GOMI, journal of Brewing Society of Japan, 494-502, 2000). Each of the obtained recombinant strains was refined in Czapek-Dox solid medium. An *Aspergillus oryzae* NS4 strain was used as a host. This strain was bred in a brewing laboratory in 1997 as described in Known Document 2, and currently, its strain which is sold in lots at National Research Institute of Brewing, which is Incorporated Administrative Agency, is available.

(7) Confirmation of Recombinant Mold-Derived GLD 10 mL of a liquid medium consisting of 2% (w/v) of Pinedex (Matsutani Chemical Industry Co., Ltd.), 1% (w/v) of tripton (Becton, Dickinson and Company), 0.5% (w/v) of potassium dihydrogenphosphate (NACALAI TESQUE, INC.), 0.05% (w/v) of magnesium sulfate heptahydrate (NACALAI TESQUE, INC.) and water was introduced into each of three test tubes (22 mm×200 mm), and autoclaved at 121° C. for 20 minutes. The transformant obtained in (6) was respectively inoculated to each cooled liquid medium, and shake-cultured at 30° C. for 4 days. After the culture, the supernatant was collected, respectively, by centrifugation, GLD activity was measured using a plate reader according to the above-mentioned method for measuring GLD activity, and as a result, the GLD activity of the present invention could be confirmed for all samples.

(8) Purification of GLD (8-1) Preparation of Crude Enzyme Liquid 150 mL of a liquid medium described in (7) was introduced into three Sakaguchi flasks with a 500 ml capacity, and autoclaved at 121° C. for 20 minutes. The transformant obtained in (6) was respectively inoculated to each cooled liquid medium, and shake-cultured at 30° C. for 3 days to obtain a seed culture liquid. 3.5 L of a medium, in which 0.005% (w/v) of chloramphenicol (NACALAI TESQUE, INC.) and an antifoaming agent were added to the same composition of the above-mentioned medium, was introduced into three jar fermentors with a 5 L capacity, and autoclaved at 121° C. for 20 minutes. 50 mL of the seed culture liquid was respectively inoculated to each cooled liquid medium, and cultured at 30° C., 400 rpm, 1 v/v/m for 4 days. After the culture, each broth was filtered with a filter cloth, the collected filtrate was centrifuged to collect the supernatant, and furthermore filtrated with a membrane filter (10 μm, Advantech Co., Ltd.) to collect the culture supernatant, respectively. Each collected culture supernatant was concentrated with an ultrafiltration membrane of 10,000 cutoff molecular weight (Millipore Corp.) to obtain crude enzyme liquids of PsGLD, PpGLD and PjGLD, respectively.

(8-2-1) Purification of PsGLD

The crude enzyme liquid of PsGLD obtained in (8-1) was adjusted to be a 60% saturated ammonium sulfate solution (pH 6.0), left to stand at 4° C. overnight, and then centrifuged to collect a supernatant. The supernatant was passed through TOYOPEARL Butyl-650C (TOSOH CORPORATION) column previously equilibrated by a 50 mM potassium phosphate buffer (pH 6.0) containing 60% saturated ammonium sulfate to adsorb the enzyme thereto. The column was washed with the same buffer, and then the enzyme was eluted by a gradient elution method from the buffer to 50 mM potassium phosphate buffer (pH 6.0) to collect an active fraction. The collected active fraction was concentrated with an ultrafiltration membrane of 10,000 cutoff molecular weight, desalinated, equilibrated with 1 mM potassium phosphate buffer (pH 6.0). Then, it was passed through a DEAE-Cellulofine A-500m (CHISSO CORPORATION) column previously equilibrated by the same buffer to adsorb the enzyme thereto. The column was washed with the same buffer, and then the enzyme was eluted by a gradient elution method from the buffer to 200 mM potassium phosphate buffer (pH 6.0) to collect an active fraction. The collected active fraction was concentrated with an ultrafiltration membrane of 8,000 cutoff molecular weight, then water substitution was performed, and the obtained sample was taken to be a purified PsGLD sample.

(8-2-2) Purification of PpGLD

The crude enzyme liquid of PpGLD obtained in (8-1) was adjusted to be a 60% saturated ammonium sulfate solution (pH 6.0), left to stand at 4° C. for an hour, and then centrifuged to collect a supernatant. The supernatant was passed through TOYOPEARL Butyl-650C (TOSOH CORPORATION) column previously equilibrated by a 50 mM potassium phosphate buffer (pH 6.0) containing 60% saturated ammonium sulfate to adsorb the enzyme thereto. The column was washed with the same buffer, and then the enzyme was eluted by a gradient elution method from the buffer to 50 mM potassium phosphate buffer (pH 6.0) containing 20% saturated ammonium sulfate to collect an active fraction. The collected active fraction was concentrated with an ultrafiltration membrane of 10,000 cutoff molecular weight, desalinated, equilibrated with 1 mM potassium phosphate buffer (pH 6.0). Then, it was passed through a DEAE-Cellulofine A-500m (CHISSO CORPORATION) column previously equilibrated by the same buffer to adsorb the enzyme thereto. The column was washed with the same buffer, and then the enzyme was eluted by a gradient elution method from the buffer to 150 mM potassium phosphate buffer (pH 6.0) to collect an active fraction. The collected active fraction was concentrated with an ultrafiltration membrane of 8,000 cutoff molecular weight, then water substitution was performed, and the resulting sample was taken to be a purified PpGLD sample.

(8-2-3) Purification of PjGLD

The crude enzyme liquid of PjGLD obtained in (8-1) was equilibrated with 5 mM potassium phosphate buffer (pH 6.0) and passed through a DEAE-Cellulofine A-500m (CHISSO CORPORATION) column previously equilibrated by the same buffer to adsorb the enzyme thereto. The column was washed with 10 mM potassium phosphate buffer (pH 6.0), and then the enzyme was eluted by a gradient elution method from the buffer to 100 mM potassium phosphate buffer (pH 6.0) to collect an active fraction. The collected active fraction was concentrated with an ultrafiltration membrane of 8,000 cutoff molecular weight, then water substitution was performed, and the obtained sample was taken to be a purified PjGLD sample.

Example 2

(Study of the Chemoenzymatic Properties of GLD of the Present Invention)

Various properties of respective purified GLDs obtained in Example 1 were evaluated.

(1) Measurement of Absorption Spectrum

GLDs of the present invention were measured for the absorption spectra at 200-700 nm before and after addition of D-glucose using a plate reader (SPECTRA MAX PLUS 384, Molecular Devices, LLC.). As a result, the absorption maximum shown around 360-380 nm and 450-460 nm disappeared by addition of D-glucose in all GLDs, thus GLDs of the present invention were proved to be flavin-conjugated proteins.

(2) Measurement of Glucose Oxidase (GOD) Activity

Search of the GOD activity of GLDs of the present invention revealed that all GLDs exhibited no GOD activity. Consequently, it was clarified that the GLDs of the present invention were hardly affected by the dissolved oxygen in the reaction system when D-glucose was quantified, because the GLDs of the present invention did not use oxygen as an electron acceptor. The GOD activity was measured by the following method.

1.00 mL of 100 mM potassium phosphate buffer (pH 7.0), 1.00 mL of 1M D-glucose, 0.10 mL of 25 mM 4-aminoantipyrine, 0.10 mL of 420 mM phenol, 0.10 mL of 100 U/mL peroxidase and 0.65 mL of ultrapure water were mixed, kept at 37° C. for 5 minutes, then 0.05 mL of enzyme sample was added, and the reaction was initiated. An increment of the absorbance at 500 nm per one minute (ΔA500) associated with progression of the enzyme reaction was measured for 5 minutes from the initiation of the reaction to calculate the GOD activity from the linear portion according to the following formula. In this measurement, for the GOD activity, an enzyme amount for generating 1 μmol of hydrogen peroxide per one minute at 37° C., pH 7.0 was defined as 1 U.

$$\text{GOD activity (U/mL)} = ((\Delta A500 - \Delta A500\text{blank}) \times 3.0 \times \text{dilution ratio of enzyme})/(10.66 \times 0.5 \times 1.0 \times 0.05)$$

Note that, 3.0 in the formula represents a liquid volume (mL) of reaction reagent+enzyme solution, 10.66 represents a molar extinction coefficient of a quinone-type pigment in the condition of this measurement, 0.5 represents a production amount of the quinone-type pigment relative to the production amount of 1 mol of hydrogen peroxide, 1.0 represents an optical path length (cm) of a cell, 0.05 represents a liquid volume (mL) of enzyme solution, and ΔA500blank represents an increment of the absorbance at 500 nm per one minute in the case that the reaction was initiated by adding a diluting solution of the enzyme instead of the enzyme solution.

(3) Substrate Specificity

For substrates, D-glucose, maltose or D-xylose of the final concentration of 50 mM were respectively used to measure the activity of each GLD corresponding to each substrate according to the method for measuring GLD activity. The results are shown in Table 1.

TABLE 1

| | Relative Activity (%) | | |
|---|---|---|---|
| | PsGLD | PpGLD | PjGLD |
| D-Glucose | 100 | 100 | 100 |
| Maltose | 1.0 | 1.1 | 0.8 |
| D-Xylose | 9.4 | 15 | 25 |

When the activity on D-glucose was taken to be 100%, the GLD of the present invention had activity of 2.0% or lower on maltose and activity of 30% or lower on D-xylose.

(4) Km Value for Glucose

According to the method for measuring GLD activity, the activity of each GLD was measured while changing the concentration of D-glucose as a substrate. The PsGLD was measured at each glucose concentration of 10, 20, 40 and 60 mM, the PpGLD was measured at each glucose concentration of 5, 10, 20 and 50 mM, and the PjGLD was measured at each glucose concentration of 1, 2, 5 and 10 mM. From each measured value of the activity, a Michaelis constant (Km value) was calculated by Hanes-Woolf plot.

As a result, the Km value for D-glucose of each GLD was 14 mM with PsGLD, 3.3 mM with PpGLD, and 3.6 mM with PjGLD. Consequently, the Km value of the GLD of the present invention is considered to be about 1.0 to 25 mM.

(5) pH Stability

After mixing so that the final concentration of each GLD was 6 U/mL and the final concentration of each buffer was 100 mM and treating for an hour at 30° C., the enzyme activity was measured with the method for measuring GLD activity. The buffer to be used was: a sodium acetate buffer (in the figure, plotted with diamond); a sodium citrate buffer (in the figure, plotted with square); a sodium phosphate buffer (in the figure, plotted with black circle); a potassium phosphate buffer (in the figure, plotted with triangle); a tris-hydrochloric acid buffer (in the figure, plotted with white circle); or a glycine-NaOH buffer (in the figure, plotted with cross). Taking the activity before treatment to be 100%, the remaining activity after the treatment was calculated as a relative value and shown in the figure as pH stability.

As a result, the relative activity of PsGLD was at least 80% at pH 3.5 to 6.8, the relative activity of PpGLD was at least 70% at pH 3.5 to 6.7 and at least 80% at pH 3.5 to 6.2, and the relative activity of PjGLD was at least 80% at pH 3.8 to 7.4. The GLDs of the present invention seemed to be stable in an acidic range.

(6) Temperature Characteristics

The activity of each GLD was measured at 25° C. or 37° C. according to the method for measuring GLD activity. The final concentration of the substrate was made to be 50 mM.

As a result, taking the activity of each GLD at 37° C. to be 100%, the relative activity of each GLD was: at least 70% for PsGLD; at least 70% for PpGLD; and at least 50% for PjGLD.

(7) Measurement of Glucose

The activity of each GLD was at each glucose concentration of 1 to 60 mM according to the method for measuring GLD activity, and the measured value for each GLD was shown in FIG. 1 as a relative activity.

As a result, it was shown that D-glucose could be quantified with the GLDs of the present invention.

The invention claimed is:

1. A glucose measuring reagent composition comprising a flavin-conjugated glucose dehydrogenase which is composed of proteins having glucose dehydrogenase activity and having an amino acid sequence selected from the group consisting of:

(a) the amino acid sequence of SEQ ID NO:8 or 9;

(b) an amino acid sequence in which 1-30 amino acids are deleted from, replaced in or added to the amino acid sequence of SEQ ID NO:8 or 9; and (c) an amino acid sequence having at least 95% identity with the amino acid sequence of SEQ ID NO:8 or 9; and one or more selected from the group consisting of bovine serum albumin (BSA), egg albumin, a sugar, a sugar alcohol not interactive with the enzyme, a carboxyl group-containing compound, an alkaline earth metal compound, an ammonium salt, and sulfate.

2. A biosensor for measuring glucose, containing a flavin-conjugated glucose dehydrogenase which is composed of proteins having glucose dehydrogenase activity and having an amino acid sequence selected from the group consisting of:

(a) the amino acid sequence of SEQ ID NO: 8 or 9;

(b) an amino acid sequence in which 1-30 amino acids are deleted from, replaced in, or added to the amino acid sequence of SEQ ID NO: 8 or 9; and (c) an amino acid sequence having at least 95% identity with the amino acid sequence of SEQ ID NO: 8 or 9.

3. The biosensor for measuring glucose according to claim 2, wherein the flavin-conjugated glucose dehydrogenase is contained in a reaction layer.

4. The biosensor for measuring glucose according to claim 2, comprising:

(i) an electrode system; and (ii) a mediator and the flavin-conjugated glucose dehydrogenase.

5. The biosensor for measuring glucose according to claim 2, wherein the flavin-conjugated glucose dehydrogenase:

(a) is able to oxidize a hydroxyl group at position 1 of glucose in the presence of an electron acceptor;

(b) is soluble;

(c) has enzymatic activity on maltose that is at most 1.5% when activity on glucose is taken to be 100%;

(d) has a molecular weight of 60 to 70 kDa; and (e) is stable at pH 3.8.

* * * * *

SEQUENCE LISTING

<160> NUMBER OF SEQ ID NOS: 18

<210> SEQ ID NO 1
<211> LENGTH: 1770
<212> TYPE: DNA
<213> ORGANISM: Penicillium sclerotiorum
<220> FEATURE:
<221> NAME/KEY: CDS
<222> LOCATION: (1)..(1770)

<400> SEQUENCE: 1

```
atg aag gga ttc tcg ggt ctc gcg ctt ctg cct ttg gca gct gca att      48
Met Lys Gly Phe Ser Gly Leu Ala Leu Leu Pro Leu Ala Ala Ala Ile
1               5                   10                  15 ccg cat gcc tcc cgt tcc aac tct gac tac gac tac atc atc gtt gga      96
Pro His Ala Ser Arg Ser Asn Ser Asp Tyr Asp Tyr Ile Ile Val Gly
                20                  25                  30 gga gga acc agt ggt ctg gtc gtc gcc aat cga cta tcc gag ctg aag     144
Gly Gly Thr Ser Gly Leu Val Val Ala Asn Arg Leu Ser Glu Leu Lys
            35                  40                  45 gat gtc aat gtc ctg gtc atc gag gcc gga ggc tcc gtt tac aac aac     192
Asp Val Asn Val Leu Val Ile Glu Ala Gly Gly Ser Val Tyr Asn Asn
    50                  55                  60 atc aac gtg aca gat gtc ggg ggc tat ggt aat gcc ttc ggt act gag     240
Ile Asn Val Thr Asp Val Gly Gly Tyr Gly Asn Ala Phe Gly Thr Glu
65                  70                  75                  80 att gac tgg gca tac gag acc gtg aag cag gaa tat gga gga aat acc     288
Ile Asp Trp Ala Tyr Glu Thr Val Lys Gln Glu Tyr Gly Gly Asn Thr
                85                  90                  95 tcg cag acc atc cga gct gga aag gct ctg gga ggt aca tcg acc atc     336
Ser Gln Thr Ile Arg Ala Gly Lys Ala Leu Gly Gly Thr Ser Thr Ile
                100                 105                 110 aac gga atg gca tac ctg cgt gct caa tcc agc cag att gac gcg tgg     384
Asn Gly Met Ala Tyr Leu Arg Ala Gln Ser Ser Gln Ile Asp Ala Trp
            115                 120                 125 gag aag atc ggc aat gag ggc tgg aac tgg gac agc ctg ctt cct tac     432
Glu Lys Ile Gly Asn Glu Gly Trp Asn Trp Asp Ser Leu Leu Pro Tyr
    130                 135                 140 ttc aag aag gga gag cag ctc cag atc cca acc cac tac tca ttc ctg     480
Phe Lys Lys Gly Glu Gln Leu Gln Ile Pro Thr His Tyr Ser Phe Leu
145                 150                 155                 160 gag gga act ggt gtc tcc tat gac ccg gct tac cat ggc tac tcc ggt     528
Glu Gly Thr Gly Val Ser Tyr Asp Pro Ala Tyr His Gly Tyr Ser Gly
                165                 170                 175 cct ctc aag gtt ggc tgg cct cag aat cag ctc aac act ggc ctt gcc     576
Pro Leu Lys Val Gly Trp Pro Gln Asn Gln Leu Asn Thr Gly Leu Ala
                180                 185                 190 cag aca ctt aac gtc aca tac aag aac atg tcg ccg gct gtt cca tac     624
Gln Thr Leu Asn Val Thr Tyr Lys Asn Met Ser Pro Ala Val Pro Tyr
            195                 200                 205 aac aat gat ccc aac ggt gga caa atg gtt gga tac tct gtc ttt cct     672
Asn Asn Asp Pro Asn Gly Gly Gln Met Val Gly Tyr Ser Val Phe Pro
    210                 215                 220 aag acg gtg aac acg gat gag aat att cgt gaa gat gct gct agg gca     720
Lys Thr Val Asn Thr Asp Glu Asn Ile Arg Glu Asp Ala Ala Arg Ala
225                 230                 235                 240 tac tac tac cct tac cag aac cga acc aac ctc cat gtg tgg ctt cac     768
Tyr Tyr Tyr Pro Tyr Gln Asn Arg Thr Asn Leu His Val Trp Leu His
                245                 250                 255 acc aat gcc aac aag ctc act tgg gag gag ggt gcc gat gca acc gca     816
Thr Asn Ala Asn Lys Leu Thr Trp Glu Glu Gly Ala Asp Ala Thr Ala
```

```
                    260                 265                 270
gag ggt gtt gag gtt acg ttc tcc aat ggc aca act tca gtc gtg aag        864
Glu Gly Val Glu Val Thr Phe Ser Asn Gly Thr Thr Ser Val Val Lys
            275                 280                 285 gcg tcg cgt gaa gtc atc ctt gca gcg ggt gca ctg aag tct ccc ctt        912
Ala Ser Arg Glu Val Ile Leu Ala Ala Gly Ala Leu Lys Ser Pro Leu
290                 295                 300 ctg ctt gag ctc tct gga gtt gga aac ccc gat gtc ctt tcc gag tac        960
Leu Leu Glu Leu Ser Gly Val Gly Asn Pro Asp Val Leu Ser Glu Tyr
305                 310                 315                 320 gac atc gag act aag atc aac ctg cca act gtt ggt gaa aac ctg cag       1008
Asp Ile Glu Thr Lys Ile Asn Leu Pro Thr Val Gly Glu Asn Leu Gln
            325                 330                 335 gat caa atg aac aac caa ctt gcc tac gac tcg aag gcc acc tac acc       1056
Asp Gln Met Asn Asn Gln Leu Ala Tyr Asp Ser Lys Ala Thr Tyr Thr
                340                 345                 350 ggc tct ccc tca tac gtc gcc tac ccc aac gcg acc gag ttg ttc cca       1104
Gly Ser Pro Ser Tyr Val Ala Tyr Pro Asn Ala Thr Glu Leu Phe Pro
            355                 360                 365 aat gcc acc gtc gtc ggt gct caa ctt ctt cgc aag ctt ccc gcc tac       1152
Asn Ala Thr Val Val Gly Ala Gln Leu Leu Arg Lys Leu Pro Ala Tyr
370                 375                 380 gca gct aag gtt gcc tcc gcc aac gga aac gtg acc cat gcc gcc gat       1200
Ala Ala Lys Val Ala Ser Ala Asn Gly Asn Val Thr His Ala Ala Asp
385                 390                 395                 400 att gag cga ttc ttc aag atc cag tgg gac ctg atc ttc aag tcc ggt       1248
Ile Glu Arg Phe Phe Lys Ile Gln Trp Asp Leu Ile Phe Lys Ser Gly
            405                 410                 415 att ccc gtc gcc gag atc ctg gtc gag cca tac agc act acc tac gac       1296
Ile Pro Val Ala Glu Ile Leu Val Glu Pro Tyr Ser Thr Thr Tyr Asp
            420                 425                 430 acc gag tac tgg gga tct gtc ccc ttc tct cgt gga aac atc cac atc       1344
Thr Glu Tyr Trp Gly Ser Val Pro Phe Ser Arg Gly Asn Ile His Ile
            435                 440                 445 tca tcc gcc gac cca acc gca gcc cct atc atc gac ccg aag tac ttc       1392
Ser Ser Ala Asp Pro Thr Ala Ala Pro Ile Ile Asp Pro Lys Tyr Phe
450                 455                 460 atg ctg gac ttc gac gtc cac tcc cag gcc cag gct gct cgt ttc atc       1440
Met Leu Asp Phe Asp Val His Ser Gln Ala Gln Ala Ala Arg Phe Ile
465                 470                 475                 480 cgc gac ctt ttc aag acc gag cct ttt gcc ggc atg gtg ggc aat gag       1488
Arg Asp Leu Phe Lys Thr Glu Pro Phe Ala Gly Met Val Gly Asn Glu
            485                 490                 495 acc act cct ggc ctg tca gcc gtt tcc tcc ggt gcc agt gat gca ggc       1536
Thr Thr Pro Gly Leu Ser Ala Val Ser Ser Gly Ala Ser Asp Ala Gly
            500                 505                 510 tgg tcg cct tac ctt aca tct aac ttc cga tcc aac ttc cac ccc att       1584
Trp Ser Pro Tyr Leu Thr Ser Asn Phe Arg Ser Asn Phe His Pro Ile
            515                 520                 525 acc act gct ggc atg atg cca aag gag att ggt ggt gtt gtc gat acc       1632
Thr Thr Ala Gly Met Met Pro Lys Glu Ile Gly Gly Val Val Asp Thr
530                 535                 540 tct ctg aag gtc tac gga act tcc aat gtc cgt gtt gtt gat gct tcc       1680
Ser Leu Lys Val Tyr Gly Thr Ser Asn Val Arg Val Val Asp Ala Ser
545                 550                 555                 560 gtt atc cca ttc cag gtc tgc ggt cat ctg cag agc act atc tat gcc       1728
Val Ile Pro Phe Gln Val Cys Gly His Leu Gln Ser Thr Ile Tyr Ala
                565                 570                 575 gtt gcc gag cgc gct gcc gac att atc aag gga aag atc tag             1770
Val Ala Glu Arg Ala Ala Asp Ile Ile Lys Gly Lys Ile
```

Val Ala Glu Arg Ala Ala Asp Ile Ile Lys Gly Lys Ile
        580                 585

<210> SEQ ID NO 2
<211> LENGTH: 589
<212> TYPE: PRT
<213> ORGANISM: Penicillium sclerotiorum

<400> SEQUENCE: 2

Met Lys Gly Phe Ser Gly Leu Ala Leu Leu Pro Leu Ala Ala Ile
1               5                   10                  15

Pro His Ala Ser Arg Ser Asn Ser Asp Tyr Asp Tyr Ile Ile Val Gly
            20                  25                  30

Gly Gly Thr Ser Gly Leu Val Val Ala Asn Arg Leu Ser Glu Leu Lys
            35                  40                  45

Asp Val Asn Val Leu Val Ile Glu Ala Gly Gly Ser Val Tyr Asn Asn
    50                  55                  60

Ile Asn Val Thr Asp Val Gly Gly Tyr Gly Asn Ala Phe Gly Thr Glu
65                  70                  75                  80

Ile Asp Trp Ala Tyr Glu Thr Val Lys Gln Glu Tyr Gly Gly Asn Thr
                85                  90                  95

Ser Gln Thr Ile Arg Ala Gly Lys Ala Leu Gly Gly Thr Ser Thr Ile
            100                 105                 110

Asn Gly Met Ala Tyr Leu Arg Ala Gln Ser Ser Gln Ile Asp Ala Trp
        115                 120                 125

Glu Lys Ile Gly Asn Glu Gly Trp Asn Trp Asp Ser Leu Leu Pro Tyr
    130                 135                 140

Phe Lys Lys Gly Glu Gln Leu Gln Ile Pro Thr His Tyr Ser Phe Leu
145                 150                 155                 160

Glu Gly Thr Gly Val Ser Tyr Asp Pro Ala Tyr His Gly Tyr Ser Gly
                165                 170                 175

Pro Leu Lys Val Gly Trp Pro Gln Asn Gln Leu Asn Thr Gly Leu Ala
            180                 185                 190

Gln Thr Leu Asn Val Thr Tyr Lys Asn Met Ser Pro Ala Val Pro Tyr
        195                 200                 205

Asn Asn Asp Pro Asn Gly Gly Gln Met Val Gly Tyr Ser Val Phe Pro
    210                 215                 220

Lys Thr Val Asn Thr Asp Glu Asn Ile Arg Glu Asp Ala Ala Arg Ala
225                 230                 235                 240

Tyr Tyr Tyr Pro Tyr Gln Asn Arg Thr Asn Leu His Val Trp Leu His
                245                 250                 255

Thr Asn Ala Asn Lys Leu Thr Trp Glu Glu Gly Ala Asp Ala Thr Ala
            260                 265                 270

Glu Gly Val Glu Val Thr Phe Ser Asn Gly Thr Thr Ser Val Val Lys
        275                 280                 285

Ala Ser Arg Glu Val Ile Leu Ala Ala Gly Ala Leu Lys Ser Pro Leu
    290                 295                 300

Leu Leu Glu Leu Ser Gly Val Gly Asn Pro Asp Val Leu Ser Glu Tyr
305                 310                 315                 320

Asp Ile Glu Thr Lys Ile Asn Leu Pro Thr Val Gly Glu Asn Leu Gln
                325                 330                 335

Asp Gln Met Asn Asn Gln Leu Ala Tyr Asp Ser Lys Ala Thr Tyr Thr
            340                 345                 350

Gly Ser Pro Ser Tyr Val Ala Tyr Pro Asn Ala Thr Glu Leu Phe Pro
        355                 360                 365

```
Asn Ala Thr Val Val Gly Ala Gln Leu Leu Arg Lys Leu Pro Ala Tyr
            370                 375                 380

Ala Ala Lys Val Ala Ser Ala Asn Gly Asn Val Thr His Ala Ala Asp
385                 390                 395                 400

Ile Glu Arg Phe Phe Lys Ile Gln Trp Asp Leu Ile Phe Lys Ser Gly
                405                 410                 415

Ile Pro Val Ala Glu Ile Leu Val Glu Pro Tyr Ser Thr Thr Tyr Asp
                420                 425                 430

Thr Glu Tyr Trp Gly Ser Val Pro Phe Ser Arg Gly Asn Ile His Ile
            435                 440                 445

Ser Ser Ala Asp Pro Thr Ala Ala Pro Ile Ile Asp Pro Lys Tyr Phe
            450                 455                 460

Met Leu Asp Phe Asp Val His Ser Gln Ala Gln Ala Ala Arg Phe Ile
465                 470                 475                 480

Arg Asp Leu Phe Lys Thr Glu Pro Phe Ala Gly Met Val Gly Asn Glu
                485                 490                 495

Thr Thr Pro Gly Leu Ser Ala Val Ser Ser Gly Ala Ser Asp Ala Gly
                500                 505                 510

Trp Ser Pro Tyr Leu Thr Ser Asn Phe Arg Ser Asn Phe His Pro Ile
            515                 520                 525

Thr Thr Ala Gly Met Met Pro Lys Glu Ile Gly Gly Val Val Asp Thr
530                 535                 540

Ser Leu Lys Val Tyr Gly Thr Ser Asn Val Arg Val Val Asp Ala Ser
545                 550                 555                 560

Val Ile Pro Phe Gln Val Cys Gly His Leu Gln Ser Thr Ile Tyr Ala
                565                 570                 575

Val Ala Glu Arg Ala Ala Asp Ile Ile Lys Gly Lys Ile
            580                 585

<210> SEQ ID NO 3
<211> LENGTH: 568
<212> TYPE: PRT
<213> ORGANISM: Penicillium sclerotiorum
<220> FEATURE:
<221> NAME/KEY: PRT
<222> LOCATION: (1)..(568)

<400> SEQUENCE: 3

Ser Asn Ser Asp Tyr Asp Tyr Ile Ile Val Gly Gly Gly Thr Ser Gly
1               5                   10                  15

Leu Val Val Ala Asn Arg Leu Ser Glu Leu Lys Asp Val Asn Val Leu
                20                  25                  30

Val Ile Glu Ala Gly Gly Ser Val Tyr Asn Asn Ile Asn Val Thr Asp
            35                  40                  45

Val Gly Gly Tyr Gly Asn Ala Phe Gly Thr Glu Ile Asp Trp Ala Tyr
        50                  55                  60

Glu Thr Val Lys Gln Glu Tyr Gly Gly Asn Thr Ser Gln Thr Ile Arg
65              70                  75                  80

Ala Gly Lys Ala Leu Gly Gly Thr Ser Thr Ile Asn Gly Met Ala Tyr
                85                  90                  95

Leu Arg Ala Gln Ser Ser Gln Ile Asp Ala Trp Glu Lys Ile Gly Asn
            100                 105                 110

Glu Gly Trp Asn Trp Asp Ser Leu Leu Pro Tyr Phe Lys Lys Gly Glu
        115                 120                 125

Gln Leu Gln Ile Pro Thr His Tyr Ser Phe Leu Glu Gly Thr Gly Val
```

```
            130                 135                 140
Ser Tyr Asp Pro Ala Tyr His Gly Tyr Ser Gly Pro Leu Lys Val Gly
145                 150                 155                 160

Trp Pro Gln Asn Gln Leu Asn Thr Gly Leu Ala Gln Thr Leu Asn Val
                165                 170                 175

Thr Tyr Lys Asn Met Ser Pro Ala Val Pro Tyr Asn Asn Asp Pro Asn
                180                 185                 190

Gly Gly Gln Met Val Gly Tyr Ser Val Phe Pro Lys Thr Val Asn Thr
                195                 200                 205

Asp Glu Asn Ile Arg Glu Asp Ala Ala Arg Ala Tyr Tyr Tyr Pro Tyr
210                 215                 220

Gln Asn Arg Thr Asn Leu His Val Trp Leu His Thr Asn Ala Asn Lys
225                 230                 235                 240

Leu Thr Trp Glu Glu Gly Ala Asp Ala Thr Ala Glu Gly Val Glu Val
                245                 250                 255

Thr Phe Ser Asn Gly Thr Thr Ser Val Val Lys Ala Ser Arg Glu Val
                260                 265                 270

Ile Leu Ala Ala Gly Ala Leu Lys Ser Pro Leu Leu Leu Glu Leu Ser
                275                 280                 285

Gly Val Gly Asn Pro Asp Val Leu Ser Glu Tyr Asp Ile Glu Thr Lys
                290                 295                 300

Ile Asn Leu Pro Thr Val Gly Glu Asn Leu Gln Asp Gln Met Asn Asn
305                 310                 315                 320

Gln Leu Ala Tyr Asp Ser Lys Ala Thr Tyr Thr Gly Ser Pro Ser Tyr
                325                 330                 335

Val Ala Tyr Pro Asn Ala Thr Glu Leu Phe Pro Asn Ala Thr Val Val
                340                 345                 350

Gly Ala Gln Leu Leu Arg Lys Leu Pro Ala Tyr Ala Ala Lys Val Ala
                355                 360                 365

Ser Ala Asn Gly Asn Val Thr His Ala Ala Asp Ile Glu Arg Phe Phe
                370                 375                 380

Lys Ile Gln Trp Asp Leu Ile Phe Lys Ser Gly Ile Pro Val Ala Glu
385                 390                 395                 400

Ile Leu Val Glu Pro Tyr Ser Thr Thr Tyr Asp Thr Glu Tyr Trp Gly
                405                 410                 415

Ser Val Pro Phe Ser Arg Gly Asn Ile His Ile Ser Ser Ala Asp Pro
                420                 425                 430

Thr Ala Ala Pro Ile Ile Asp Pro Lys Tyr Phe Met Leu Asp Phe Asp
                435                 440                 445

Val His Ser Gln Ala Gln Ala Ala Arg Phe Ile Arg Asp Leu Phe Lys
450                 455                 460

Thr Glu Pro Phe Ala Gly Met Val Gly Asn Glu Thr Thr Pro Gly Leu
465                 470                 475                 480

Ser Ala Val Ser Ser Gly Ala Ser Asp Ala Gly Trp Ser Pro Tyr Leu
                485                 490                 495

Thr Ser Asn Phe Arg Ser Asn Phe His Pro Ile Thr Thr Ala Gly Met
                500                 505                 510

Met Pro Lys Glu Ile Gly Gly Val Val Asp Thr Ser Leu Lys Val Tyr
                515                 520                 525

Gly Thr Ser Asn Val Arg Val Val Asp Ala Ser Val Ile Pro Phe Gln
                530                 535                 540

Val Cys Gly His Leu Gln Ser Thr Ile Tyr Ala Val Ala Glu Arg Ala
545                 550                 555                 560
```

Ala Asp Ile Ile Lys Gly Lys Ile
                565

<210> SEQ ID NO 4
<211> LENGTH: 1779
<212> TYPE: DNA
<213> ORGANISM: Penicillium paneum
<220> FEATURE:
<221> NAME/KEY: CDS
<222> LOCATION: (1)..(1779)

<400> SEQUENCE: 4

```
atg cgc agc ctc att ggt ctt gca ctg ctt cca cta gcg gtt gca gtt    48
Met Arg Ser Leu Ile Gly Leu Ala Leu Leu Pro Leu Ala Val Ala Val
1               5                  10                  15 ccc cat gcc tca cac aag tca gag tcg act tac gac tat gtc att gtt    96
Pro His Ala Ser His Lys Ser Glu Ser Thr Tyr Asp Tyr Val Ile Val
            20                  25                  30 gga ggt ggc acc agt ggc ctc gtc gtt gca aac cga ttg tcc gag aac   144
Gly Gly Gly Thr Ser Gly Leu Val Val Ala Asn Arg Leu Ser Glu Asn
        35                  40                  45 aag gac acc act gtc ctg gtg atc gaa gcc ggc ggc tcc gtc tat aac   192
Lys Asp Thr Thr Val Leu Val Ile Glu Ala Gly Gly Ser Val Tyr Asn
    50                  55                  60 aac cca aat gtg acc gac act ctc gga tac ggc aaa gcg ttc gat aca   240
Asn Pro Asn Val Thr Asp Thr Leu Gly Tyr Gly Lys Ala Phe Asp Thr
65                  70                  75                  80 gac att gac tgg gcc tac aaa acg aca gac caa gaa tat gcc ggt ggt   288
Asp Ile Asp Trp Ala Tyr Lys Thr Thr Asp Gln Glu Tyr Ala Gly Gly
                85                  90                  95 tcc cca caa aca atg cgt gcc gga aag gca ctc gga gga aca tcg acc   336
Ser Pro Gln Thr Met Arg Ala Gly Lys Ala Leu Gly Gly Thr Ser Thr
            100                 105                 110 atc aac ggc atg gcg tac ctc cgt gcc cag gca gct cag atc gac gcg   384
Ile Asn Gly Met Ala Tyr Leu Arg Ala Gln Ala Ala Gln Ile Asp Ala
        115                 120                 125 tgg gag acc atc ggc aat aag ggc tgg aac tgg aag act ctg ctc ccc   432
Trp Glu Thr Ile Gly Asn Lys Gly Trp Asn Trp Lys Thr Leu Leu Pro
    130                 135                 140 tac ttc aaa aag ggt gag caa ttg caa gat ccg gca cag tac cca ttt   480
Tyr Phe Lys Lys Gly Glu Gln Leu Gln Asp Pro Ala Gln Tyr Pro Phe
145                 150                 155                 160 ttg gac gga tca ggt gtt gct ttt gat ccg gcc tac cac ggc ttt acg   528
Leu Asp Gly Ser Gly Val Ala Phe Asp Pro Ala Tyr His Gly Phe Thr
                165                 170                 175 ggc cca ctg aag gtt ggc tgg tct tca aca cag ttg aac gat ggt ctt   576
Gly Pro Leu Lys Val Gly Trp Ser Ser Thr Gln Leu Asn Asp Gly Leu
            180                 185                 190 gct cag gaa ttg aac act acc tat caa aac ctc gat gtt cct gtt cag   624
Ala Gln Glu Leu Asn Thr Thr Tyr Gln Asn Leu Asp Val Pro Val Gln
        195                 200                 205 tac aac cgg gat ccc aat ggc gga gat atg gtt gga tac agc ctg tac   672
Tyr Asn Arg Asp Pro Asn Gly Gly Asp Met Val Gly Tyr Ser Leu Tyr
    210                 215                 220 cct aag acg gtt gat tct gag ctc aac atc cgg gag gat gct gct cgt   720
Pro Lys Thr Val Asp Ser Glu Leu Asn Ile Arg Glu Asp Ala Ala Arg
225                 230                 235                 240 gcc tac tat tat ccc tac cag aac aga acc aat ctc ctt gtc tgg ctc   768
Ala Tyr Tyr Tyr Pro Tyr Gln Asn Arg Thr Asn Leu Leu Val Trp Leu
                245                 250                 255
```

| | |
|---|---|
| aac aca cac gcc aac aag att acc tgg aag gat ggc cat gag gtc act<br>Asn Thr His Ala Asn Lys Ile Thr Trp Lys Asp Gly His Glu Val Thr<br>                260                        265                      270 | 816 |
| gcg aat ggt gtc gag gtc act ttt tcc aat ggc aca acc acc gtg gtt<br>Ala Asn Gly Val Glu Val Thr Phe Ser Asn Gly Thr Thr Thr Val Val<br>        275                        280                        285 | 864 |
| aag gct act cgt gaa gta atc ctc gct gct ggt gca ttg aaa tct ccc<br>Lys Ala Thr Arg Glu Val Ile Leu Ala Ala Gly Ala Leu Lys Ser Pro<br>290                        295                        300 | 912 |
| gtt ctg ctc gaa ctt tcc ggc gtt gga aac cca gag att ctt tcc aag<br>Val Leu Leu Glu Leu Ser Gly Val Gly Asn Pro Glu Ile Leu Ser Lys<br>305                        310                        315                        320 | 960 |
| tac gga atc gcc act aaa att aac ctg cca act gtc ggc gaa aat ctg<br>Tyr Gly Ile Ala Thr Lys Ile Asn Leu Pro Thr Val Gly Glu Asn Leu<br>                325                        330                        335 | 1008 |
| cag gac caa atg aac aat ggc ctc cag ttc gac tcg aag aaa acc tac<br>Gln Asp Gln Met Asn Asn Gly Leu Gln Phe Asp Ser Lys Lys Thr Tyr<br>        340                        345                        350 | 1056 |
| agc agc aac aag agt gcc gac tac gtc gcc tac ccc tca gca gct cag<br>Ser Ser Asn Lys Ser Ala Asp Tyr Val Ala Tyr Pro Ser Ala Ala Gln<br>                355                        360                        365 | 1104 |
| ctc ttc ccc aac tcc aca gca ctc gga gcc gaa ctt ctt cgc gag ctt<br>Leu Phe Pro Asn Ser Thr Ala Leu Gly Ala Glu Leu Leu Arg Glu Leu<br>370                        375                        380 | 1152 |
| ccc gct tat gca gcg caa gtt gca tcc gcc aac ggc aac atc act aaa<br>Pro Ala Tyr Ala Ala Gln Val Ala Ser Ala Asn Gly Asn Ile Thr Lys<br>385                        390                        395                        400 | 1200 |
| gcc cgc gac ata tat cgc ttc ttt aag atc cag tgg gat ctg atc ttt<br>Ala Arg Asp Ile Tyr Arg Phe Phe Lys Ile Gln Trp Asp Leu Ile Phe<br>                        405                        410                        415 | 1248 |
| aaa tcc ggt att cct gtt gcg gag atc ctg ctg tcg gcc tct gga acc<br>Lys Ser Gly Ile Pro Val Ala Glu Ile Leu Leu Ser Ala Ser Gly Thr<br>                  420                        425                        430 | 1296 |
| tca tac agc agc gaa tac tgg ggt tct gtt cca ttc tct cgc ggc aac<br>Ser Tyr Ser Ser Glu Tyr Trp Gly Ser Val Pro Phe Ser Arg Gly Asn<br>                435                        440                        445 | 1344 |
| gtt cac ctc tct tcc gcg gac ccc acc gcg gcg gct atc att gac ccc<br>Val His Leu Ser Ser Ala Asp Pro Thr Ala Ala Ala Ile Ile Asp Pro<br>450                        455                        460 | 1392 |
| aag tac ttc atg ctg gac ttt gat cta cat tct cag gtg cag gcg gcg<br>Lys Tyr Phe Met Leu Asp Phe Asp Leu His Ser Gln Val Gln Ala Ala<br>465                        470                        475                        480 | 1440 |
| cga ttt att cgt gag atc ttc aaa act gag cca ttt gct gat atg gct<br>Arg Phe Ile Arg Glu Ile Phe Lys Thr Glu Pro Phe Ala Asp Met Ala<br>                        485                        490                        495 | 1488 |
| ggt gct gaa acc agt cct ggt ctt tcc act gtt gct gct ggt gct gat<br>Gly Ala Glu Thr Ser Pro Gly Leu Ser Thr Val Ala Ala Gly Ala Asp<br>        500                        505                        510 | 1536 |
| gat gag ggc tgg gct gat ttc atc aag ggt caa tac cga tca aac ttc<br>Asp Glu Gly Trp Ala Asp Phe Ile Lys Gly Gln Tyr Arg Ser Asn Phe<br>                515                        520                        525 | 1584 |
| cac ccg att acc aca gct gct atg ctt ccc aag gag att ggt ggt gtt<br>His Pro Ile Thr Thr Ala Ala Met Leu Pro Lys Glu Ile Gly Gly Val<br>530                        535                        540 | 1632 |
| gtc gac acg tcg ctg aag gtt tac gga acc tca aat gtt cgt gtt gta<br>Val Asp Thr Ser Leu Lys Val Tyr Gly Thr Ser Asn Val Arg Val Val<br>545                        550                        555                        560 | 1680 |
| gat gct tcc gtc atg cct ttc cag gtc tgc ggt cac ctt caa agc acc<br>Asp Ala Ser Val Met Pro Phe Gln Val Cys Gly His Leu Gln Ser Thr<br>                        565                        570                        575 | 1728 |

```
gtg tat gcg gtt gct gag cgt gcg gcc gat atc atc aag gcg tgc tac    1776
Val Tyr Ala Val Ala Glu Arg Ala Ala Asp Ile Ile Lys Ala Cys Tyr
            580                 585                 590 taa                                                                1779
```

<210> SEQ ID NO 5
<211> LENGTH: 592
<212> TYPE: PRT
<213> ORGANISM: Penicillium paneum

<400> SEQUENCE: 5

```
Met Arg Ser Leu Ile Gly Leu Ala Leu Leu Pro Leu Ala Val Ala Val
1               5                   10                  15

Pro His Ala Ser His Lys Ser Glu Ser Thr Tyr Asp Tyr Val Ile Val
            20                  25                  30

Gly Gly Gly Thr Ser Gly Leu Val Ala Asn Arg Leu Ser Glu Asn
        35                  40                  45

Lys Asp Thr Thr Val Leu Val Ile Glu Ala Gly Gly Ser Val Tyr Asn
50                  55                  60

Asn Pro Asn Val Thr Asp Thr Leu Gly Tyr Gly Lys Ala Phe Asp Thr
65                  70                  75                  80

Asp Ile Asp Trp Ala Tyr Lys Thr Thr Asp Gln Glu Tyr Ala Gly Gly
                85                  90                  95

Ser Pro Gln Thr Met Arg Ala Gly Lys Ala Leu Gly Gly Thr Ser Thr
            100                 105                 110

Ile Asn Gly Met Ala Tyr Leu Arg Ala Gln Ala Ala Gln Ile Asp Ala
        115                 120                 125

Trp Glu Thr Ile Gly Asn Lys Gly Trp Asn Trp Lys Thr Leu Leu Pro
130                 135                 140

Tyr Phe Lys Lys Gly Glu Gln Leu Gln Asp Pro Ala Gln Tyr Pro Phe
145                 150                 155                 160

Leu Asp Gly Ser Gly Val Ala Phe Asp Pro Ala Tyr His Gly Phe Thr
                165                 170                 175

Gly Pro Leu Lys Val Gly Trp Ser Ser Thr Gln Leu Asn Asp Gly Leu
            180                 185                 190

Ala Gln Glu Leu Asn Thr Thr Tyr Gln Asn Leu Asp Val Pro Val Gln
        195                 200                 205

Tyr Asn Arg Asp Pro Asn Gly Gly Asp Met Val Gly Tyr Ser Leu Tyr
210                 215                 220

Pro Lys Thr Val Asp Ser Glu Leu Asn Ile Arg Glu Asp Ala Ala Arg
225                 230                 235                 240

Ala Tyr Tyr Tyr Pro Tyr Gln Asn Arg Thr Asn Leu Leu Val Trp Leu
                245                 250                 255

Asn Thr His Ala Asn Lys Ile Thr Trp Lys Asp Gly His Glu Val Thr
            260                 265                 270

Ala Asn Gly Val Glu Val Thr Phe Ser Asn Gly Thr Thr Thr Val Val
        275                 280                 285

Lys Ala Thr Arg Glu Val Ile Leu Ala Ala Gly Ala Leu Lys Ser Pro
290                 295                 300

Val Leu Leu Glu Leu Ser Gly Val Gly Asn Pro Glu Ile Leu Ser Lys
305                 310                 315                 320

Tyr Gly Ile Ala Thr Lys Ile Asn Leu Pro Thr Val Gly Glu Asn Leu
                325                 330                 335

Gln Asp Gln Met Asn Asn Gly Leu Gln Phe Asp Ser Lys Lys Thr Tyr
```

```
        340                 345                 350
Ser Ser Asn Lys Ser Ala Asp Tyr Val Ala Tyr Pro Ser Ala Ala Gln
            355                 360                 365
Leu Phe Pro Asn Ser Thr Ala Leu Gly Ala Glu Leu Leu Arg Glu Leu
        370                 375                 380
Pro Ala Tyr Ala Ala Gln Val Ala Ser Ala Asn Gly Asn Ile Thr Lys
385                 390                 395                 400
Ala Arg Asp Ile Tyr Arg Phe Phe Lys Ile Gln Trp Asp Leu Ile Phe
                405                 410                 415
Lys Ser Gly Ile Pro Val Ala Glu Ile Leu Leu Ser Ala Ser Gly Thr
            420                 425                 430
Ser Tyr Ser Ser Glu Tyr Trp Gly Ser Val Pro Phe Ser Arg Gly Asn
        435                 440                 445
Val His Leu Ser Ser Ala Asp Pro Thr Ala Ala Ile Ile Asp Pro
        450                 455                 460
Lys Tyr Phe Met Leu Asp Phe Asp Leu His Ser Gln Val Gln Ala Ala
465                 470                 475                 480
Arg Phe Ile Arg Glu Ile Phe Lys Thr Glu Pro Phe Ala Asp Met Ala
                485                 490                 495
Gly Ala Glu Thr Ser Pro Gly Leu Ser Thr Val Ala Ala Gly Ala Asp
            500                 505                 510
Asp Glu Gly Trp Ala Asp Phe Ile Lys Gly Gln Tyr Arg Ser Asn Phe
        515                 520                 525
His Pro Ile Thr Thr Ala Ala Met Leu Pro Lys Glu Ile Gly Gly Val
        530                 535                 540
Val Asp Thr Ser Leu Lys Val Tyr Gly Thr Ser Asn Val Arg Val Val
545                 550                 555                 560
Asp Ala Ser Val Met Pro Phe Gln Val Cys Gly His Leu Gln Ser Thr
                565                 570                 575
Val Tyr Ala Val Ala Glu Arg Ala Ala Asp Ile Ile Lys Ala Cys Tyr
            580                 585                 590

<210> SEQ ID NO 6
<211> LENGTH: 570
<212> TYPE: PRT
<213> ORGANISM: Penicillium paneum
<220> FEATURE:
<221> NAME/KEY: PRT
<222> LOCATION: (1)..(570)

<400> SEQUENCE: 6

Ser Glu Ser Thr Tyr Asp Tyr Val Ile Val Gly Gly Thr Ser Gly
1               5                   10                  15
Leu Val Val Ala Asn Arg Leu Ser Glu Asn Lys Asp Thr Thr Val Leu
            20                  25                  30
Val Ile Glu Ala Gly Gly Ser Val Tyr Asn Asn Pro Asn Val Thr Asp
        35                  40                  45
Thr Leu Gly Tyr Gly Lys Ala Phe Asp Thr Asp Ile Asp Trp Ala Tyr
    50                  55                  60
Lys Thr Thr Asp Gln Glu Tyr Ala Gly Gly Ser Pro Gln Thr Met Arg
65                  70                  75                  80
Ala Gly Lys Ala Leu Gly Gly Thr Ser Thr Ile Asn Gly Met Ala Tyr
                85                  90                  95
Leu Arg Ala Gln Ala Ala Gln Ile Asp Ala Trp Glu Thr Ile Gly Asn
            100                 105                 110
```

```
Lys Gly Trp Asn Trp Lys Thr Leu Leu Pro Tyr Phe Lys Lys Gly Glu
            115                 120                 125
Gln Leu Gln Asp Pro Ala Gln Tyr Pro Phe Leu Asp Gly Ser Gly Val
        130                 135                 140
Ala Phe Asp Pro Ala Tyr His Gly Phe Thr Gly Pro Leu Lys Val Gly
145                 150                 155                 160
Trp Ser Ser Thr Gln Leu Asn Asp Gly Leu Ala Gln Glu Leu Asn Thr
                165                 170                 175
Thr Tyr Gln Asn Leu Asp Val Pro Val Gln Tyr Asn Arg Asp Pro Asn
            180                 185                 190
Gly Gly Asp Met Val Gly Tyr Ser Leu Tyr Pro Lys Thr Val Asp Ser
        195                 200                 205
Glu Leu Asn Ile Arg Glu Asp Ala Ala Arg Ala Tyr Tyr Tyr Pro Tyr
    210                 215                 220
Gln Asn Arg Thr Asn Leu Leu Val Trp Leu Asn Thr His Ala Asn Lys
225                 230                 235                 240
Ile Thr Trp Lys Asp Gly His Glu Val Thr Ala Asn Gly Val Glu Val
                245                 250                 255
Thr Phe Ser Asn Gly Thr Thr Thr Val Val Lys Ala Thr Arg Glu Val
            260                 265                 270
Ile Leu Ala Ala Gly Ala Leu Lys Ser Pro Val Leu Leu Glu Leu Ser
        275                 280                 285
Gly Val Gly Asn Pro Glu Ile Leu Ser Lys Tyr Gly Ile Ala Thr Lys
    290                 295                 300
Ile Asn Leu Pro Thr Val Gly Glu Asn Leu Gln Asp Gln Met Asn Asn
305                 310                 315                 320
Gly Leu Gln Phe Asp Ser Lys Lys Thr Tyr Ser Ser Asn Lys Ser Ala
                325                 330                 335
Asp Tyr Val Ala Tyr Pro Ser Ala Ala Gln Leu Phe Pro Asn Ser Thr
            340                 345                 350
Ala Leu Gly Ala Glu Leu Leu Arg Glu Leu Pro Ala Tyr Ala Ala Gln
        355                 360                 365
Val Ala Ser Ala Asn Gly Asn Ile Thr Lys Ala Arg Asp Ile Tyr Arg
    370                 375                 380
Phe Phe Lys Ile Gln Trp Asp Leu Ile Phe Lys Ser Gly Ile Pro Val
385                 390                 395                 400
Ala Glu Ile Leu Leu Ser Ala Ser Gly Thr Ser Tyr Ser Ser Glu Tyr
                405                 410                 415
Trp Gly Ser Val Pro Phe Ser Arg Gly Asn Val His Leu Ser Ser Ala
            420                 425                 430
Asp Pro Thr Ala Ala Ile Ile Asp Pro Lys Tyr Phe Met Leu Asp
        435                 440                 445
Phe Asp Leu His Ser Gln Val Gln Ala Ala Arg Phe Ile Arg Glu Ile
    450                 455                 460
Phe Lys Thr Glu Pro Phe Ala Asp Met Ala Gly Ala Glu Thr Ser Pro
465                 470                 475                 480
Gly Leu Ser Thr Val Ala Ala Gly Ala Asp Asp Glu Gly Trp Ala Asp
                485                 490                 495
Phe Ile Lys Gly Gln Tyr Arg Ser Asn Phe His Pro Ile Thr Thr Ala
            500                 505                 510
Ala Met Leu Pro Lys Glu Ile Gly Gly Val Val Asp Thr Ser Leu Lys
        515                 520                 525
Val Tyr Gly Thr Ser Asn Val Arg Val Val Asp Ala Ser Val Met Pro
```

-continued

```
                530                    535                    540
            Phe Gln Val Cys Gly His Leu Gln Ser Thr Val Tyr Ala Val Ala Glu
            545                    550                    555                    560

Arg Ala Ala Asp Ile Ile Lys Ala Cys Tyr
                                565                    570

<210> SEQ ID NO 7
<211> LENGTH: 1761
<212> TYPE: DNA
<213> ORGANISM: Penicillium janthinellum
<220> FEATURE:
<221> NAME/KEY: CDS
<222> LOCATION: (1)..(1761)

<400> SEQUENCE: 7 atg ctg gtc ccc aag act ctt tct tcc gtt tac ttt gcg gcc gtg gct        48
Met Leu Val Pro Lys Thr Leu Ser Ser Val Tyr Phe Ala Ala Val Ala
1               5                   10                  15 gct gcc gct tcc tat gac tat atc gtc gtg gga gga ggt act ggt ggt        96
Ala Ala Ala Ser Tyr Asp Tyr Ile Val Val Gly Gly Gly Thr Gly Gly
                20                  25                  30 ctc gtc att gcc aac cgc ctg tct gag agc tcg agc agg tcg gtt ctg       144
Leu Val Ile Ala Asn Arg Leu Ser Glu Ser Ser Ser Arg Ser Val Leu
            35                  40                  45 atc gtt gag cgc ggt gac tct gtc ctt ggc aac acc gaa gtc tct gat       192
Ile Val Glu Arg Gly Asp Ser Val Leu Gly Asn Thr Glu Val Ser Asp
        50                  55                  60 tcc aac gcc tat gga gcg gcc ttt ggc tcg tcg att gac tat gcc tat       240
Ser Asn Ala Tyr Gly Ala Ala Phe Gly Ser Ser Ile Asp Tyr Ala Tyr
65                  70                  75                  80 cag tct att gcc cag caa tat gct gga ggc cgc gtc cag act ttg cgc       288
Gln Ser Ile Ala Gln Gln Tyr Ala Gly Gly Arg Val Gln Thr Leu Arg
                85                  90                  95 gcc ggc aag gct ctc ggt ggt acc agt acc atc aac ggc atg gcc tac       336
Ala Gly Lys Ala Leu Gly Gly Thr Ser Thr Ile Asn Gly Met Ala Tyr
                100                 105                 110 acc cgc gcc cag gat gtc cag atc gac gcc tgg ggt aat atg gga aac       384
Thr Arg Ala Gln Asp Val Gln Ile Asp Ala Trp Gly Asn Met Gly Asn
            115                 120                 125 tct ggc tgg agt tgg aag agt ttg ttg ccc tac tat cag aag agc gag       432
Ser Gly Trp Ser Trp Lys Ser Leu Leu Pro Tyr Tyr Gln Lys Ser Glu
        130                 135                 140 tct ttc cag gtt cct acc tcg gcc cag tac gat gcc ggt gcg aac tat       480
Ser Phe Gln Val Pro Thr Ser Ala Gln Tyr Asp Ala Gly Ala Asn Tyr
145                 150                 155                 160 gtc gcc tca tac aac ggc gaa tct ggc cct ctg ctg gtg ggt tgg acc       528
Val Ala Ser Tyr Asn Gly Glu Ser Gly Pro Leu Leu Val Gly Trp Thr
                165                 170                 175 tac gac atg cag aac agt agc att cac act tcg ttg aat gag acc tac       576
Tyr Asp Met Gln Asn Ser Ser Ile His Thr Ser Leu Asn Glu Thr Tyr
                180                 185                 190 gag cat ttg ggt atc agc tat gtt ccg gat gtc aac ggt ggc aag atg       624
Glu His Leu Gly Ile Ser Tyr Val Pro Asp Val Asn Gly Gly Lys Met
            195                 200                 205 cac ggc tac tcc atg ttc ccc cgt act gtc aac cgt gcc cag cag ctt       672
His Gly Tyr Ser Met Phe Pro Arg Thr Val Asn Arg Ala Gln Gln Leu
        210                 215                 220 cgt gag gat gct gct cgt gcc tac tac tac ccc gtc gac agc aga cca       720
Arg Glu Asp Ala Ala Arg Ala Tyr Tyr Tyr Pro Val Asp Ser Arg Pro
225                 230                 235                 240
```

```
aac ttg tct gtt atg ctt aac act acc gga aac cgt att gtc tgg gag        768
Asn Leu Ser Val Met Leu Asn Thr Thr Gly Asn Arg Ile Val Trp Glu
            245                 250                 255 tct tcg gtc agc tct ggt agc cct gca gtt gcc act ggc atc gaa gtg        816
Ser Ser Val Ser Ser Gly Ser Pro Ala Val Ala Thr Gly Ile Glu Val
        260                 265                 270 acc cac agc gat ggc acc acg gaa acc att act gct ctc cag gag gtc        864
Thr His Ser Asp Gly Thr Thr Glu Thr Ile Thr Ala Leu Gln Glu Val
                275                 280                 285 att ctc tct gct ggt tcc ttg atc agc cct gct att ctg gag cgc tct        912
Ile Leu Ser Ala Gly Ser Leu Ile Ser Pro Ala Ile Leu Glu Arg Ser
    290                 295                 300 ggc gtt gga aac cct gcg gtt ctt gct cag cac aac att cct gtg gtc        960
Gly Val Gly Asn Pro Ala Val Leu Ala Gln His Asn Ile Pro Val Val
305                 310                 315                 320 gtg aac ctg acc acc gtc ggc gag aac ctc caa gac cag acc aac aca       1008
Val Asn Leu Thr Thr Val Gly Glu Asn Leu Gln Asp Gln Thr Asn Thr
                325                 330                 335 gag ctc atc tac acc agc cct gtc aat tac act ggc gca gga acc tat       1056
Glu Leu Ile Tyr Thr Ser Pro Val Asn Tyr Thr Gly Ala Gly Thr Tyr
            340                 345                 350 ctg ggc cac ccc act gtg tcc gat atc ttc ggt tcc aac atc acc aat       1104
Leu Gly His Pro Thr Val Ser Asp Ile Phe Gly Ser Asn Ile Thr Asn
        355                 360                 365 gtc gcc aac gat gtc aag aac aac ttg ccc aac tat gcc gcg aag gtc       1152
Val Ala Asn Asp Val Lys Asn Asn Leu Pro Asn Tyr Ala Ala Lys Val
370                 375                 380 tct gcc gca agc aac gga acc atg agc gag tcc aac ctc ttg tac ctg       1200
Ser Ala Ala Ser Asn Gly Thr Met Ser Glu Ser Asn Leu Leu Tyr Leu
385                 390                 395                 400 ttc aaa atg caa tac gac atc att ttc gag aac ccg acc ccc att gcc       1248
Phe Lys Met Gln Tyr Asp Ile Ile Phe Glu Asn Pro Thr Pro Ile Ala
                405                 410                 415 gag ctg ctg gtc acc ccc aag ggc gac aag ttc tac tcc gag tac tgg       1296
Glu Leu Leu Val Thr Pro Lys Gly Asp Lys Phe Tyr Ser Glu Tyr Trp
            420                 425                 430 gga ctg atg ccc ttc gcc cgt gga aat gtt cac att gcc tct acc gac       1344
Gly Leu Met Pro Phe Ala Arg Gly Asn Val His Ile Ala Ser Thr Asp
        435                 440                 445 ccc ctg gcg cag cct gtc atc aac cct aac tac atg atg ctt gag ttt       1392
Pro Leu Ala Gln Pro Val Ile Asn Pro Asn Tyr Met Met Leu Glu Phe
450                 455                 460 gat atg cag cag cag att ggc tct gcc aag ttc ctt cgc acc atc tac       1440
Asp Met Gln Gln Gln Ile Gly Ser Ala Lys Phe Leu Arg Thr Ile Tyr
465                 470                 475                 480 atg acc gct cct atg agc aac gag acc act ggc gag gcc tcg cct ggt       1488
Met Thr Ala Pro Met Ser Asn Glu Thr Thr Gly Glu Ala Ser Pro Gly
                485                 490                 495 tac act acc gtc cca gct gat gcc acc gat gcc cag tgg gct acc tgg       1536
Tyr Thr Thr Val Pro Ala Asp Ala Thr Asp Ala Gln Trp Ala Thr Trp
            500                 505                 510 atc aac agt gcc tcc cgc tca aat ttc cat ccc gtc ggc acc gcc gcc       1584
Ile Asn Ser Ala Ser Arg Ser Asn Phe His Pro Val Gly Thr Ala Ala
        515                 520                 525 atg atg ccc cgt tcc atg ggt ggt gtc gtc gac act aac ttg gtg gtc       1632
Met Met Pro Arg Ser Met Gly Gly Val Val Asp Thr Asn Leu Val Val
530                 535                 540 tac gac acc aag aac gtc cgc gtc gtt gat gcc tct atc ctt cct ttc       1680
Tyr Asp Thr Lys Asn Val Arg Val Val Asp Ala Ser Ile Leu Pro Phe
545                 550                 555                 560
```

```
cag gtc tgt ggt cat ttg acc tct act atc tac gct gtg gcc gag cgt    1728
Gln Val Cys Gly His Leu Thr Ser Thr Ile Tyr Ala Val Ala Glu Arg
                565                 570                 575 att gcc gac cag atc aag gct gga agc gtt taa                        1761
Ile Ala Asp Gln Ile Lys Ala Gly Ser Val
            580                 585
```

<210> SEQ ID NO 8
<211> LENGTH: 586
<212> TYPE: PRT
<213> ORGANISM: Penicillium janthinellum

<400> SEQUENCE: 8

```
Met Leu Val Pro Lys Thr Leu Ser Ser Val Tyr Phe Ala Ala Val Ala
1               5                   10                  15

Ala Ala Ala Ser Tyr Asp Tyr Ile Val Val Gly Gly Gly Thr Gly Gly
            20                  25                  30

Leu Val Ile Ala Asn Arg Leu Ser Glu Ser Ser Arg Ser Val Leu
        35                  40                  45

Ile Val Glu Arg Gly Asp Ser Val Leu Gly Asn Thr Glu Val Ser Asp
    50                  55                  60

Ser Asn Ala Tyr Gly Ala Ala Phe Gly Ser Ser Ile Asp Tyr Ala Tyr
65                  70                  75                  80

Gln Ser Ile Ala Gln Gln Tyr Ala Gly Gly Arg Val Gln Thr Leu Arg
                85                  90                  95

Ala Gly Lys Ala Leu Gly Gly Thr Ser Thr Ile Asn Gly Met Ala Tyr
            100                 105                 110

Thr Arg Ala Gln Asp Val Gln Ile Asp Ala Trp Gly Asn Met Gly Asn
        115                 120                 125

Ser Gly Trp Ser Trp Lys Ser Leu Leu Pro Tyr Tyr Gln Lys Ser Glu
    130                 135                 140

Ser Phe Gln Val Pro Thr Ser Ala Gln Tyr Asp Ala Gly Ala Asn Tyr
145                 150                 155                 160

Val Ala Ser Tyr Asn Gly Glu Ser Gly Pro Leu Leu Val Gly Trp Thr
                165                 170                 175

Tyr Asp Met Gln Asn Ser Ser Ile His Thr Ser Leu Asn Glu Thr Tyr
            180                 185                 190

Glu His Leu Gly Ile Ser Tyr Val Pro Asp Val Asn Gly Gly Lys Met
        195                 200                 205

His Gly Tyr Ser Met Phe Pro Arg Thr Val Asn Arg Ala Gln Gln Leu
    210                 215                 220

Arg Glu Asp Ala Ala Arg Ala Tyr Tyr Tyr Pro Val Asp Ser Arg Pro
225                 230                 235                 240

Asn Leu Ser Val Met Leu Asn Thr Thr Gly Asn Arg Ile Val Trp Glu
                245                 250                 255

Ser Ser Val Ser Ser Gly Ser Pro Ala Val Ala Thr Gly Ile Glu Val
            260                 265                 270

Thr His Ser Asp Gly Thr Thr Glu Thr Ile Thr Ala Leu Gln Glu Val
        275                 280                 285

Ile Leu Ser Ala Gly Ser Leu Ile Ser Pro Ala Ile Leu Glu Arg Ser
    290                 295                 300

Gly Val Gly Asn Pro Ala Val Leu Ala Gln His Asn Ile Pro Val Val
305                 310                 315                 320

Val Asn Leu Thr Thr Val Gly Glu Asn Leu Gln Asp Gln Thr Asn Thr
                325                 330                 335
```

```
Glu Leu Ile Tyr Thr Ser Pro Val Asn Tyr Thr Gly Ala Gly Thr Tyr
            340                 345                 350

Leu Gly His Pro Thr Val Ser Asp Ile Phe Gly Ser Asn Ile Thr Asn
            355                 360                 365

Val Ala Asn Asp Val Lys Asn Asn Leu Pro Asn Tyr Ala Ala Lys Val
370                 375                 380

Ser Ala Ala Ser Asn Gly Thr Met Ser Glu Ser Asn Leu Leu Tyr Leu
385                 390                 395                 400

Phe Lys Met Gln Tyr Asp Ile Ile Phe Glu Asn Pro Thr Pro Ile Ala
                405                 410                 415

Glu Leu Leu Val Thr Pro Lys Gly Asp Lys Phe Tyr Ser Glu Tyr Trp
            420                 425                 430

Gly Leu Met Pro Phe Ala Arg Gly Asn Val His Ile Ala Ser Thr Asp
            435                 440                 445

Pro Leu Ala Gln Pro Val Ile Asn Pro Asn Tyr Met Met Leu Glu Phe
450                 455                 460

Asp Met Gln Gln Gln Ile Gly Ser Ala Lys Phe Leu Arg Thr Ile Tyr
465                 470                 475                 480

Met Thr Ala Pro Met Ser Asn Glu Thr Thr Gly Glu Ala Ser Pro Gly
                485                 490                 495

Tyr Thr Thr Val Pro Ala Asp Ala Thr Asp Ala Gln Trp Ala Thr Trp
            500                 505                 510

Ile Asn Ser Ala Ser Arg Ser Asn Phe His Pro Val Gly Thr Ala Ala
            515                 520                 525

Met Met Pro Arg Ser Met Gly Gly Val Val Asp Thr Asn Leu Val Val
            530                 535                 540

Tyr Asp Thr Lys Asn Val Arg Val Val Asp Ala Ser Ile Leu Pro Phe
545                 550                 555                 560

Gln Val Cys Gly His Leu Thr Ser Thr Ile Tyr Ala Val Ala Glu Arg
                565                 570                 575

Ile Ala Asp Gln Ile Lys Ala Gly Ser Val
                580                 585

<210> SEQ ID NO 9
<211> LENGTH: 567
<212> TYPE: PRT
<213> ORGANISM: Penicillium janthinellum
<220> FEATURE:
<221> NAME/KEY: PRT
<222> LOCATION: (1)..(567)

<400> SEQUENCE: 9

Ser Tyr Asp Tyr Ile Val Val Gly Gly Thr Gly Gly Leu Val Ile
1               5                   10                  15

Ala Asn Arg Leu Ser Glu Ser Ser Arg Ser Val Leu Ile Val Glu
            20                  25                  30

Arg Gly Asp Ser Val Leu Gly Asn Thr Glu Val Ser Ser Asn Ala
            35                  40                  45

Tyr Gly Ala Ala Phe Gly Ser Ser Ile Asp Tyr Ala Tyr Gln Ser Ile
    50                  55                  60

Ala Gln Gln Tyr Ala Gly Arg Val Gln Thr Leu Arg Ala Gly Lys
65                  70                  75                  80

Ala Leu Gly Gly Thr Ser Thr Ile Asn Gly Met Ala Tyr Thr Arg Ala
                85                  90                  95

Gln Asp Val Gln Ile Asp Ala Trp Gly Asn Met Gly Asn Ser Gly Trp
```

```
                100                 105                 110
Ser Trp Lys Ser Leu Leu Pro Tyr Tyr Gln Lys Ser Glu Ser Phe Gln
            115                 120                 125

Val Pro Thr Ser Ala Gln Tyr Asp Ala Gly Ala Asn Tyr Val Ala Ser
        130                 135                 140

Tyr Asn Gly Glu Ser Gly Pro Leu Leu Val Gly Trp Thr Tyr Asp Met
145                 150                 155                 160

Gln Asn Ser Ser Ile His Thr Ser Leu Asn Glu Thr Tyr Glu His Leu
                165                 170                 175

Gly Ile Ser Tyr Val Pro Asp Val Asn Gly Lys Met His Gly Tyr
            180                 185                 190

Ser Met Phe Pro Arg Thr Val Asn Arg Ala Gln Gln Leu Arg Glu Asp
        195                 200                 205

Ala Ala Arg Ala Tyr Tyr Pro Val Asp Ser Arg Pro Asn Leu Ser
    210                 215                 220

Val Met Leu Asn Thr Thr Gly Asn Arg Ile Val Trp Glu Ser Ser Val
225                 230                 235                 240

Ser Ser Gly Ser Pro Ala Val Ala Thr Gly Ile Glu Val Thr His Ser
                245                 250                 255

Asp Gly Thr Thr Glu Thr Ile Thr Ala Leu Gln Glu Val Ile Leu Ser
            260                 265                 270

Ala Gly Ser Leu Ile Ser Pro Ala Ile Leu Glu Arg Ser Gly Val Gly
        275                 280                 285

Asn Pro Ala Val Leu Ala Gln His Asn Ile Pro Val Val Asn Leu
    290                 295                 300

Thr Thr Val Gly Glu Asn Leu Gln Asp Gln Thr Asn Thr Glu Leu Ile
305                 310                 315                 320

Tyr Thr Ser Pro Val Asn Tyr Thr Gly Ala Gly Thr Tyr Leu Gly His
                325                 330                 335

Pro Thr Val Ser Asp Ile Phe Gly Ser Asn Ile Thr Asn Val Ala Asn
            340                 345                 350

Asp Val Lys Asn Asn Leu Pro Asn Tyr Ala Ala Lys Val Ser Ala Ala
        355                 360                 365

Ser Asn Gly Thr Met Ser Glu Ser Asn Leu Leu Tyr Leu Phe Lys Met
    370                 375                 380

Gln Tyr Asp Ile Ile Phe Glu Asn Pro Thr Pro Ile Ala Glu Leu Leu
385                 390                 395                 400

Val Thr Pro Lys Gly Asp Lys Phe Tyr Ser Glu Tyr Trp Gly Leu Met
                405                 410                 415

Pro Phe Ala Arg Gly Asn Val His Ile Ala Ser Thr Asp Pro Leu Ala
            420                 425                 430

Gln Pro Val Ile Asn Pro Asn Tyr Met Met Leu Glu Phe Asp Met Gln
        435                 440                 445

Gln Gln Ile Gly Ser Ala Lys Phe Leu Arg Thr Ile Tyr Met Thr Ala
    450                 455                 460

Pro Met Ser Asn Glu Thr Thr Gly Glu Ala Ser Pro Gly Tyr Thr Thr
465                 470                 475                 480

Val Pro Ala Asp Ala Thr Asp Ala Gln Trp Ala Thr Trp Ile Asn Ser
                485                 490                 495

Ala Ser Arg Ser Asn Phe His Pro Val Gly Thr Ala Ala Met Met Pro
            500                 505                 510

Arg Ser Met Gly Gly Val Val Asp Thr Asn Leu Val Val Tyr Asp Thr
        515                 520                 525
```

Lys Asn Val Arg Val Val Asp Ala Ser Ile Leu Pro Phe Gln Val Cys
    530                 535                 540

Gly His Leu Thr Ser Thr Ile Tyr Ala Val Ala Glu Arg Ile Ala Asp
545                 550                 555                 560

Gln Ile Lys Ala Gly Ser Val
            565

<210> SEQ ID NO 10
<211> LENGTH: 34
<212> TYPE: DNA
<213> ORGANISM: Artificial Sequence
<220> FEATURE:
<223> OTHER INFORMATION: primer:S158-Ori

<400> SEQUENCE: 10
ccgcagctcg tcaaaatgaa gggattctcg ggtc                                34

<210> SEQ ID NO 11
<211> LENGTH: 30
<212> TYPE: DNA
<213> ORGANISM: Artificial Sequence
<220> FEATURE:
<223> OTHER INFORMATION: primer:S158-R-1st

<400> SEQUENCE: 11
gttcatttag atctttccct tgataatgtc                                     30

<210> SEQ ID NO 12
<211> LENGTH: 39
<212> TYPE: DNA
<213> ORGANISM: Artificial Sequence
<220> FEATURE:
<223> OTHER INFORMATION: primer:S158-R-2nd

<400> SEQUENCE: 12
gttacgcttc tagagcatgc gttcatttag atctttccc                           39

<210> SEQ ID NO 13
<211> LENGTH: 36
<212> TYPE: DNA
<213> ORGANISM: Artificial Sequence
<220> FEATURE:
<223> OTHER INFORMATION: primer:S1268-A.o

<400> SEQUENCE: 13
ccggctggac gggccgttcc ccatgcctca cacaag                              36

<210> SEQ ID NO 14
<211> LENGTH: 29
<212> TYPE: DNA
<213> ORGANISM: Artificial Sequence
<220> FEATURE:
<223> OTHER INFORMATION: primer:S1268-R-1st

<400> SEQUENCE: 14
gttcatttag tagcacgcct tgatgatat                                      29

<210> SEQ ID NO 15
<211> LENGTH: 38
<212> TYPE: DNA
<213> ORGANISM: Artificial Sequence
<220> FEATURE:
<223> OTHER INFORMATION: primer:S1268-R-2nd

<400> SEQUENCE: 15

```
gttacgcttc tagagcatgc gttcatttag tagcacgc                                    38

<210> SEQ ID NO 16
<211> LENGTH: 34
<212> TYPE: DNA
<213> ORGANISM: Artificial Sequence
<220> FEATURE:
<223> OTHER INFORMATION: primer:T475-Ori

<400> SEQUENCE: 16
ccgcagctcg tcaaaatgct ggtccccaag actc                                        34

<210> SEQ ID NO 17
<211> LENGTH: 28
<212> TYPE: DNA
<213> ORGANISM: Artificial Sequence
<220> FEATURE:
<223> OTHER INFORMATION: primer:T475-R-1st

<400> SEQUENCE: 17
gttcatttaa acgcttccag ccttgatc                                               28

<210> SEQ ID NO 18
<211> LENGTH: 39
<212> TYPE: DNA
<213> ORGANISM: Artificial Sequence
<220> FEATURE:
<223> OTHER INFORMATION: primer:T475-R-2nd

<400> SEQUENCE: 18
gttacgcttc tagagcatgc gttcatttaa acgcttcca                                   39
```